United States Patent [19]

Furukawa et al.

[11] Patent Number: 5,976,833
[45] Date of Patent: Nov. 2, 1999

[54] METHOD FOR ANIMAL CELL CULTURE

[75] Inventors: Kazuaki Furukawa, Tatebayashi; Kazuhiro Ohsuye, Ohta, both of Japan

[73] Assignee: Suntory Limited, Osaka, Japan

[21] Appl. No.: 08/716,533

[22] Filed: Sep. 19, 1996

[30]  Foreign Application Priority Data

Sep. 19, 1995 [JP] Japan .................................. 7-263633

[51] Int. Cl.⁶ .................................................. C12N 15/00
[52] U.S. Cl. ..................... 435/69.1; 435/71.1; 435/243; 435/320.1; 435/352; 435/358; 435/440; 435/464
[58] Field of Search ........................... 435/68, 240, 69.1, 435/320.1, 69.7, 172.3, 71.1, 243, 352, 358, 440, 464; 536/23.2

[56]  References Cited

U.S. PATENT DOCUMENTS

| 4,357,422 | 11/1982 | Giard et al. ............................... 436/68 |
| 5,270,040 | 12/1993 | Bang et al. . | |

FOREIGN PATENT DOCUMENTS

| 0 501 692 A2 | 9/1992 | European Pat. Off. . |
| 7-31495 | 2/1995 | Japan . |
| WO 82/00661 | 3/1998 | WIPO . |

OTHER PUBLICATIONS

Ozturk et al, "Growth, Metabolic, and Antibody Production Kinetics of Hybridoma Cell Culture: 2. Effects of Serum Concentration, Dissolved Oxygen Concentration, and Medium pH in a Batch Reactor," *Biotechol. Prog.*, vol. 7, pp. 481–494 (1991).
Otto–Wilheim Merten, "Batch production and growth kinetics of hybridomas," *Cytotechnolgy*, vol. 1, pp. 113–121 (1988).
T. Craig Seamans et al., "Kinetics of Growth and Antibody Production by a Hybridoma Cell Line in a Perfusion Culture," *Journal of Fermentation and Bioengineering*, vol. 70, No. 4, pp. 241–245 (1990).
W.M. Miller et al., "A Kinetic Analysis of Hybridoma Growth and Metabolism in Batch and Continuous Suspension Culture: Effect of Nutrient Concentration, Dilution Rate, and pH," *Biotechnology and Bioengineering*, vol. 32, pp. 947–965 (1988).
Nigel Jenkins et al, "Tempature Control of Growth and Productivity in Mutant Chinese Hamster Ovary Cells Synthesizing a Recombinant Protein", *Biotechnology and Bioengineering*, vol. 42, pp. 1029–1036 (1993).
Vilcek et al, "Stabilization of Interferon Messenger RNA Activity by Treatment of Cells with Metabolic Inhibitors and Lowering of the Incubation Temperature", *Proc. Nat. Acad. Sci. USA*, vol. 70, No. 12, Part II, pp. 3909–3913 (Dec. 1973).
Kojima et al, "Enhanced Production of Interferon by Temperature Shift–Down from 37 C to 35 C in Rabbit Cell Cultures Stimulated with Newcastle Disease Virus," *Japan. J. Microbiol.*, vol. 18(3), pp. 217–222 (1974).

Giard et al, "Examination of Parameters Affecting Human Interferon Production with Microcarrier–Grown Fibroblast Cells," *Antimicrobial Agents and Chemotherapy*, vol. 18, No. 1, pp. 130–136 (1980).
Giard et al, "Effect of Temperature on the Production of Human Fibroblast Interferon (41411)," *Proceedings of the Society for Experimental Biology and Medicine*, 170, pp. 155–159 (1982).
Musgrave et al, "The Enhancement of α–Inferferon Production by Manipulation Temperature," *J. Interferon Res.*, vol. 11, Suppl. 1, pp. S211 (1991).
Sureshkumar et al, "The Influence of Temperature on a Mouse–Mouse Hybridoma Growth and Monoclonal Antibody Production," *Biotechnology and Bioengineering*, vol. 37, pp. 292–295 (1991).
Bloemkolk et al, "Effect of Temperature on Hybridoma Cell Cycle and MAb Production," *Biotechnology and Bioengineering*, vol. 40, pp. 427–431 (1992).
Kurano et al, "Growth behavior of Chinese hamster ovary cells in a compact loop bioreactor: 1. Effects of physical and chemical environments," *Journal of Biotechnology*, vol. 15, pp. 101–111 (1990).
Jenkins et al, "Temperature Control of Growth and Productivity in Mutant Chinese Hamster Ovary Cells Synthesizing a Recombinant Protein," *Biotechnololgy and Bioengineering*, vol. 42, pp. 1029–1036 (1993).
Takagi et al, "Comparison of the optimal culture conditions for cell growth and tissue plasminogen activator production by human embryo lung cells on microcarriers," *Appl Microbiol. Biotechnol.*, vol. 41, pp. 565–570 (1994).
Borth et al, "Growth and production kinetics of human x mouse and mouse hybridoma cells at reduced temperature and serum content," *Journal of Biotechnology*, vol. 25, pp. 319–331 (1992).
Reuveny et al, "Factors affecting cell growth and monoclonal antibody production in stirred reactors," *Journal of Immunological Methods*, vol. 86, pp. 53–59 (1986).
Weidemann et al, "Low temperature cultivation—A step towards process optimisation," *Cytotechnology*, vol. 15, pp. 111–116 (1994).
Beaudry, G.A. et al. 1990 J. of Biol. Chem. 265(29):17694–17699.
Ray, M.V.L. et. al. 1993 Bio/Technology 11:64–70.
Borth et al. Journal of Biotechnology. vol. 25, pp. 319–331, 1992.
Kirinaka et al. Appl. Microbiol. Biotechnol. vol. 41, pp. 591–596, 1994.
Weidemann et al. Cytotechnology. vol. pp. 111–116, 1994.
Beaudry et al. The Journal of Biological Chemistry. vol. 265, No. 29, pp. 17694–17699, 1990.

*Primary Examiner*—Nancy Degen
*Assistant Examiner*—Irem Yucel
*Attorney, Agent, or Firm*—Burns, Doane, Swecker & Mathis, L.L.P.

[57]  ABSTRACT

The object of the present invention is to provide a method for improving productivity in the production of useful substances by animal cells. The present invention discloses a method for animal cell culture to produce a desired substance, comprising the steps of (1) culturing animal cells at a temperature at which the animal cells can grow; and (2) culturing the animal cells at a lower temperature.

11 Claims, 18 Drawing Sheets

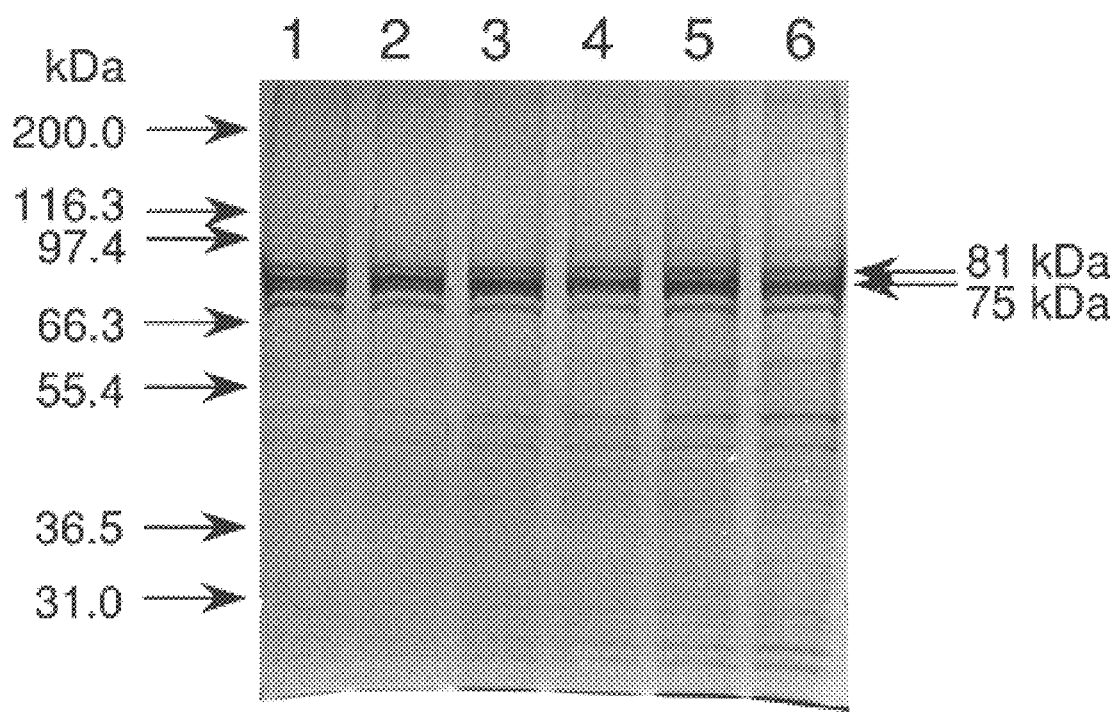

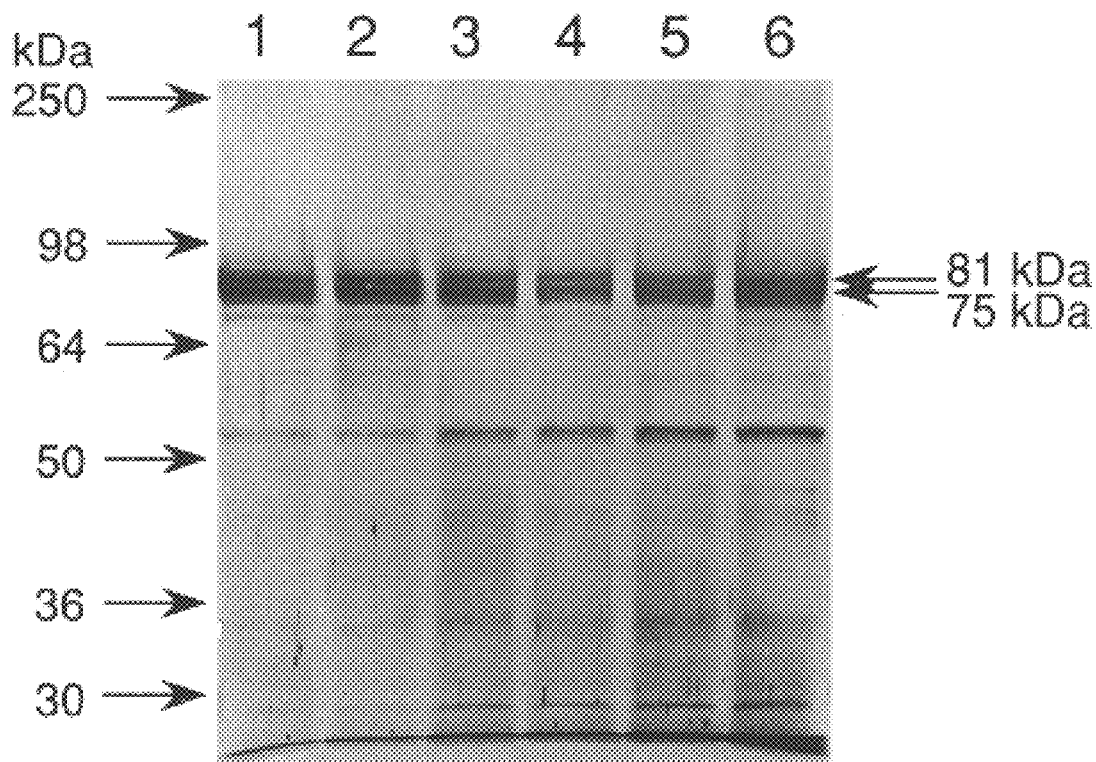

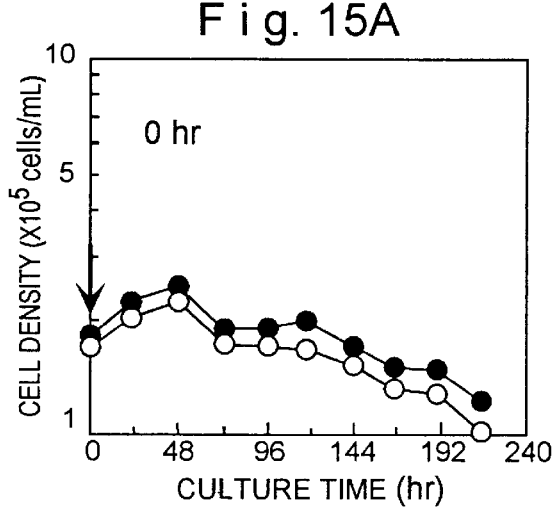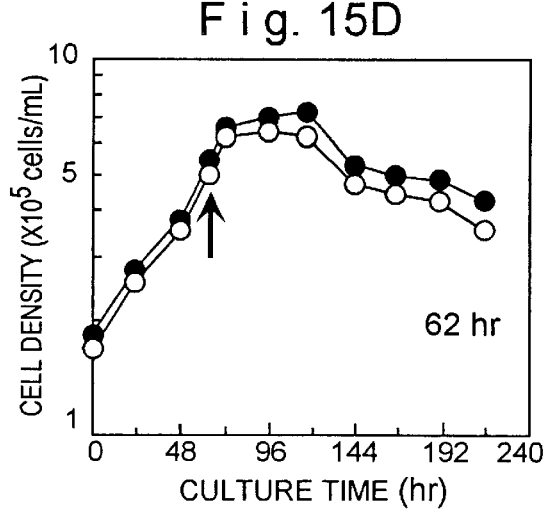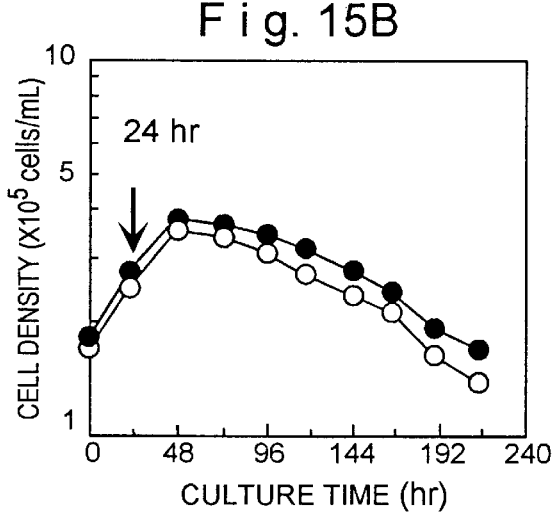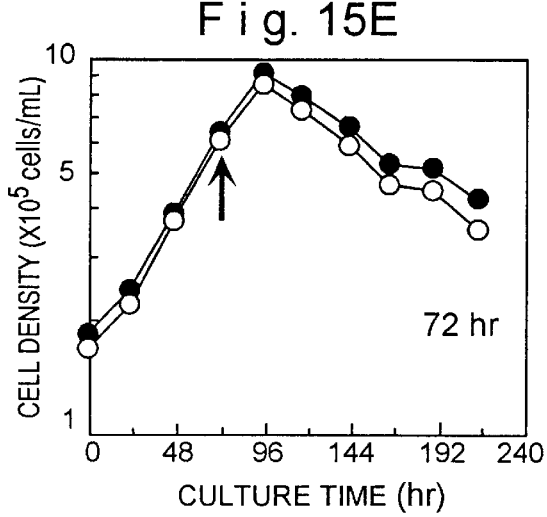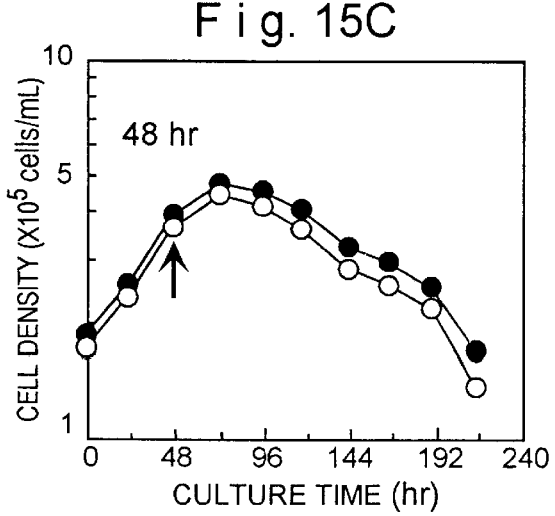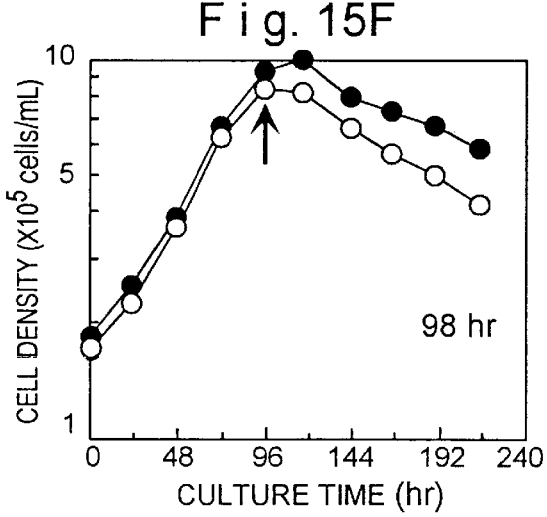

METHOD FOR ANIMAL CELL CULTURE

BACKGROUND OF INVENTION

1. Field of Invention

The present invention relates to a method of producing protein or peptide by the culture of recombinant cells.

2. Related Art

Numerous useful substances are produced by culturing microorganisms or animal cells.

Although the production of useful substances using microorganisms such as E. coli is advantageous in terms of the amount produced per medium or productivity per cell, such a method cannot be applied in cases wherein the target protein has a high molecular weight and has a too complex steric structure to be refolded, or in cases of substances whose physiological activity is exhibited only after modification of such as sugar chains.

Animal cells are typically used to produce such proteins. Examples of known animal cells include CHO-K1 (Chinese hamster ovary cell: ATCC CCL-61), CHO-K1-derived dihydro folate reductase (DHFR) gene-deficient line, hybridomas constructed by fusing a parent cell (myeloma, etc.) with a useful substance-producing normal cell (lymphocyte, etc.), C127I (mouse mammary tumor cells: ATCC CRL-1616), BHK-21(C-13) (baby hamster kidney cell: ATCC CCL-10) and Vero (African green monkey kidney cell: ATCC CCL-81).

However, shortcomings of animals cells when compared with microorganisms include a slow growth rate, expensive media and low production per medium and productivity per cell. The use of large-scale culture vessels, basic culture conditions (incubation temperature, dissolved oxygen concentration, pH, etc.), media (serum-free media, protein-free media, etc.), medium additives (butyric acid, dimethylsulfoxide (DMSO), hydrocortizone, etc.) and increased density of cultured cells are being examined as ways of dealing with these shortcomings.

In the culturing of animals cells, the incubation temperature is almost always 37° C. However, since incubation temperature is considered to have an effect on cell growth as well as the metabolism of various substances, optimum temperature is an indispensable element of substance production by cell culturing.

The effect of incubation temperature was first studied in the 1970's in the production of interferon. In addition, there are also several reports of studies in monoclonal antibody-producing hybridomas starting in the 1980's.

With respect to the production of interferon, by treating normal fibroblasts, Burkitt's lymphoma cells (Namalwa cells), rabbit kidney cells (RK13), other lymphoblast-like cells and so forth with various chemicals such as poly I (polyinosinic acid), poly C (polycytidylic acid), cycloheximide, actinomycin D and butyric acid, or viruses such as Sendai virus, it is possible to create a system that induces production of interferon. It is reported that in this system, the amount of interferon can be increased by lowering the incubation temperature (Proc. Nat. Acad. Sci. USA, Vol. 70, No. 12, Part II, pp.3909–3913, 1973; Japan J. Microbiol., Vol. 18(3), 217–222, 1974; Antimicrob. Agents Chemother., Vol. 18, No. 1, p.130–136, 1980; Proceedings of the Society for Experimental Biology and Medicine, 170, 155–159, 1982; J. Interferon Res. 11, Suppl. 1, S211, 1991; and, Japanese Unexamined Patent Publication No. 7-31495).

However, since the methods indicated there require complex procedures for inducing production, large-volume production on an industrial scale is difficult. Moreover, this is not a culturing method that can be universally applied to animal cells.

With respect to monoclonal antibody-producing hybridomas, it has been reported that in the case of lowering the incubation temperature, although a high viability is maintained for a long time and glucose consumption is reduced, monoclonal antibody productivity decreases (Biotechnology and Bioengineering, Vol. 37, pp.292–295, 1991). It has also been reported that although the number of cells in the G1 stage of the cell cycle increases, antibody productivity per cell does not change, with maximum cell growth and maximum antibody production occurring during culture at 37° C. (Biotechnology and Bioengineering, Vol. 40, pp.427–431, 1992), thus indicating different interpretations depending on the cell line used.

Antibody production in hybridomas is thought to be affected by the properties of the parent cell line such as myeloma as well as the antibody-producing lymphocytes that are fused with it. Thus results are thought to differ depending on the cell line used.

On the other hand, in CHO cells that are commonly used as host cells for gene recombination, although there are reports that the optimum temperature for cell growth is 37° C. (Journal of Biotechnology, 15, 101–111, 1990), the optimum temperature for substance production is completely unknown.

In addition, with respect to the effect of incubation temperature on gene recombinant cells, although there is a report that a temperature-sensitive mutant strain derived from CHO cells (optimum temperature for cell growth: 34° C., for substance production: 39° C.) was constructed and applied for substance production (Biotechnology and Bioengineering, Vol. 42, pp.1029–1036, 1993), since a temperature-sensitive strain was used, no assumptions can be made regarding the effect of incubation temperature on normal gene recombinant cells.

Thus, there is currently very little information available relating to the effect of incubation temperature on gene recombinant cells. In addition, the previously illustrated reports involved studies of the effects of incubation temperature from the aspect of cell growth or substance productivity. However, when considering substance production by cell culturing, since it is also necessary to consider the following purification process as well as the culturing itself, studies should focus on more comprehensive aspects including consumption of media components, contaminating proteins and so forth in addition to cell growth and substance productivity. Thus, with respect to animal cells in general, findings regarding the effects of incubation temperature can be said to be insufficient at present.

SUMMARY OF INVENTION

In comparing substance production costs between conventional animal cell culturing methods and microorganism culturing methods, costs for the animal cells continue to remain at a high level. Thus, efforts are continuously being sought to achieve reduced costs. The object of the present invention is to provide a culturing method for realizing greater efficiency (reduced costs) in substance production by animal cell culturing.

Accordingly the present invention provide a method for culturing animal cells to produce a derived product, comprising the step of:

(1) culturing the animal cells at a temperature at which the animal cells can grow; and then (2) culturing the animal cells at a lower temperature.

BRIEF EXPLANATION OF DRAWINGS

FIG. 9 is an electrophoresis pattern on SDS-PAGE of the culture supernatant (equivalent to 45 units of AE) of 3μ-1S cells cultured at various temperatures.

FIG. 10 shows the result of Western blot analysis of the culture supernatant (equivalent to 45 units of AE) of 3μ-1S cells cultured at various temperatures.

FIG. 15 shows graphs that indicate the changes in cell density when temperature was shifted at various times during batch culture of 3μ-1S cells. The black and white circles in the graphs indicate total cell density and viable cell density, respectively, while the arrows indicate the times at which the temperature was shifted.

Figure 1A:
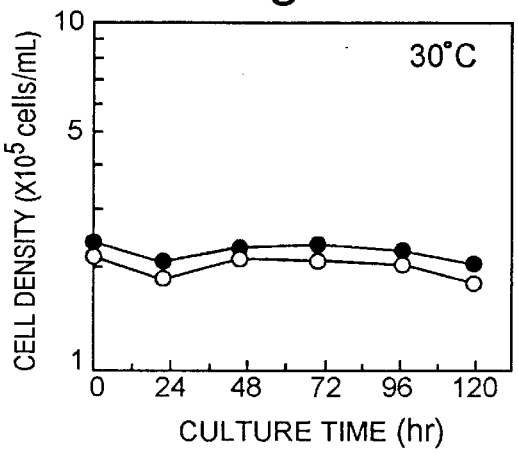
FIG. 1 indicates growth curves of 3μ-1S cells at various culturing temperatures. The black and white circles in the graphs indicate total cell density and viable cell density, respectively.
Figure 1D:
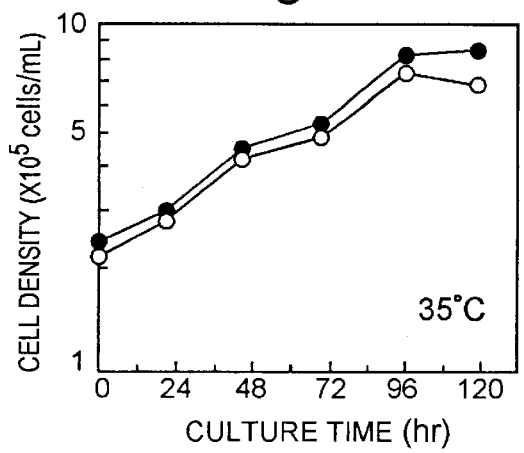
Figure 1B:
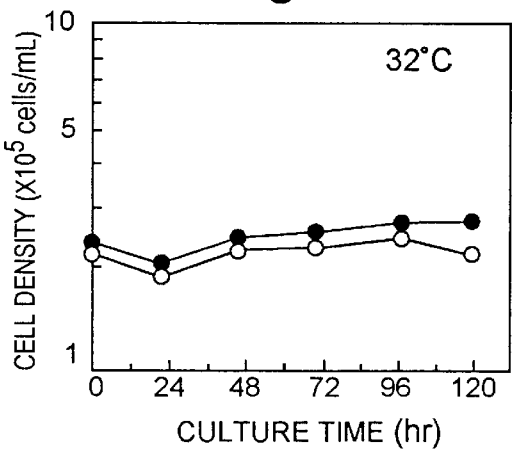
Figure 1E:
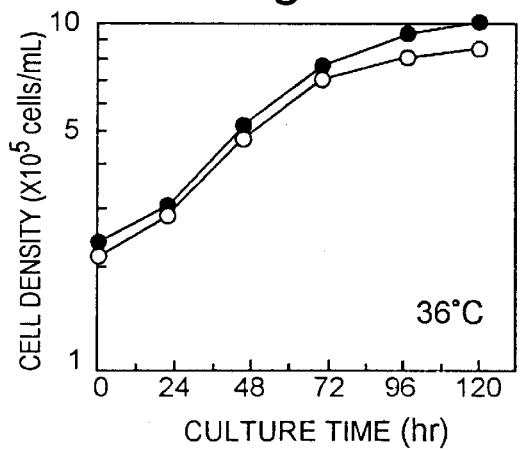
Figure 1C:
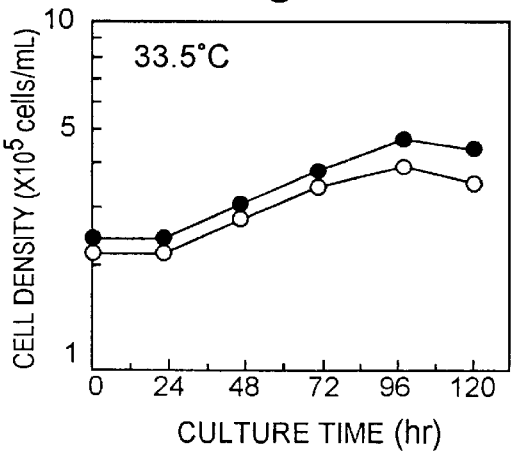
Figure 1F:
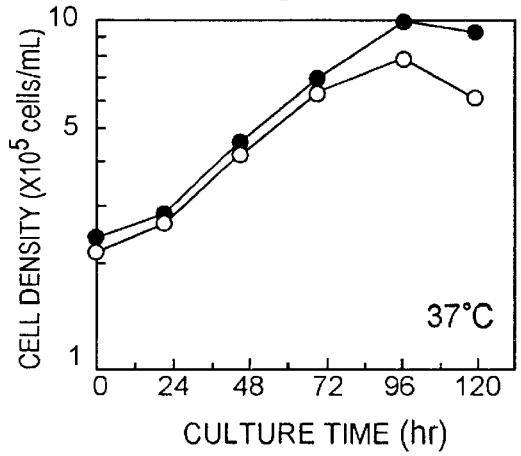

In the production of a desired substance by cell culture, since the objective is to isolate of the desired substance that is produced, in order to achieve a high productivity of the substance, in addition to improving the substance productivity of the cells, it is also necessary to reduce an amount of contaminating substances such as proteins and so forth derived from metabolic by-products and from cell contents in the culture. The present inventors conducted in-depth studies from various aspects on culture temperature as one of the basic culture conditions, and as a result established an animal cell culture method that enables efficient protein production.

The present inventors conducted studies on the effect of culturing temperature on 3μ-1S cells, which are suspended CHO cells producing an amidating enzyme (AE) (Animal Cell Technology: Basic & Applied Aspects, Vol. 5, 493–499 (1993)), from the aspects of cell growth, cell viability, substance (AE) productivity, medium consumption and purity of the target substance (AE) in the culture supernatant.

As a result, in culturing at under 37° C., although cell growth was inhibited, it was found that a high cell viability was maintained, cellular productivity of the AE increased, consumption of nutrients (almost amino acids, glucose) in the medium was reduced, release of impurities from the cells such as metabolic by-products and cell contents was suppressed, and there was essentially no change in the AE produced.

These phenomena show that a significant increase in the productivity of desired substance by animal cell culture is possible by lowering the culture temperature provided an adequate number of cells is obtained.

In the production of a substance by culturing at low temperatures, it is proposed that in a batch culture cells are cultured at a temperature optimal for growth (36–38° C.), followed by lowering the culturing temperature; and in a continuous culture, the cells are cultured at a temperature optimal for cell growth until a high cell density is reached, followed by lowering the culturing temperature. The present inventors confirmed that substance productivity is dramatically increased by using a culturing temperature of under 37° C. in batch culture and high-density continuous culture, thereby leading to completion of the present invention.

"Protein" in the present invention refers to protein or peptide. Although examples of proteins that can be produced according to the present invention include AE, tissue plasminogen activator (TPA), erythropoietin (EPO), various colony stimulating factors (G-CSF, M-CSF and GM-CSF), various interleukins (IL-1 through IL-12), various Interferons (IFN-α, β and γ), tumor necrosis factor (TNF), thrombopoietin (TPO) and stem cell factor (SCF), the proteins are not limited to these examples. In addition, there is also the possibility of producing currently unknown useful proteins by applying the present invention in the future.

Although examples of animal cells that can be used in the present invention include non-recombinant animal cells that produce useful proteins, hybridomas constructed by fusion with a parent cell line having unlimited growth capability, and animal cells transformed with a gene coding for a desired protein (gene recombinant cells), and any cells wherein sufficient production of the target substance is observed by lowering a culture temperature are preferable. Gene recombinant cells and hybridomas, in particular, of the present invention can be efficient be obtained by performing screening based on said property at the stage of establishing cell line. In addition, suspension cells or adhesive cells can also be used.

Cell culture can be carried out in any culture vessel or culture apparatus conventionally used in animal cell culture. Although Petri dishes, T-flasks and spinner flasks used on a laboratory scale, culture apparatuses equipped with cell separator using filters, gravity, centrifugal force and so forth used in high-density culturing of suspended cells, culturing apparatuses using harboring carriers such as micro-carriers or hollow fibers that are used mainly for high-density culture of adhesive cells, or bioreactors for industrial production and so forth can be used, the vessels or apparatuses are not limited to these examples.

Any medium ordinary used in culturing of animal cells may be used for the basal medium. Although either medium containing serum or that not containing serum may be used, serum-free media, which contain insulin, transferrin and so forth instead of serum, are preferable. Protein-free media are the most preferable.

With respect to the culture temperature, although it is possible to culture at a low temperature from the start of culturing, it is preferable to first culture at a temperature that enables growth (primary culturing temperature), and then after obtaining a sufficient number of cells, culturing at a low temperature (secondary culturing temperature). The primary culturing temperature referred to here is preferably the temperature optimal for growth, and if the cells are derived from homiothermal animals, a temperature of 36–38° C. is common, while a temperature of 37° C. is the most common. Although the secondary culturing temperature is below the primary culturing temperature and below 37° C., it is preferably 30–35° C. and most preferably 30–32° C.

In addition, the temperature lowering time (temperature shift time) is preferably the time at which substance productivity can be adequately increased. In batch culture, it is possible to determine the optimum temperature shift time by performing the experiment as indicated in Reference Example 2 dependent on the cell line used. The temperature shift time in continuous culture is preferably the time at which cell density becomes sufficiently high. However, since the cell density that can be achieved in continuous culture varies according to the properties of the cell line used (suspendability, adhesion, etc.), various culture conditions (medium, pH, DO, stirring rate, shape of culture vessel, circulation rate, perfusion rate, etc.) and so forth, it cannot be limited within a narrow range, and is typically $10^6$ to $10^8$ cells/mL.

EXAMPLES

The following Examples provide a detailed explanation of the present invention. However, the present invention is not limited to these embodiments.

Reference Example 1
Establishment of MTX 3 μM-Resistant Strain 9C

The E. coli k12 strain used in this Reference Example 1, which have been transformed with plasmids pKDPXA457 and pKDPXA799 Bgl II, are respectively named E. coli SBM 300 and E. coli SBM 301, and were deposited at the Institute of Bioscience and Human Technology, Agency of Industrial Science and Technology as FERM BP-2235 and FERM BP-2236.

pKDPXA457 and pKDPXA799 Bgl II were respectively introduced into CHO cells derived from Chinese hamster ovary cell deficient for the dihydrofolate reductase (dhfr) gene (abbreviated as CHO dhfr⁻ cells, named CHO dhfr⁻ Cell SBM 306, and deposited at the Institute of bioscience and Human Technology, Agency of Industrial Science and Technology as FERM BP-2441) (Hanaka, S. et al., Mol. Cell. Biol. 7, 2578–2587, 1987) by calcium phosphate coprecipitation.

Namely, CHO dhfr⁻ cells, which were subcultured in Minimum Essential Medium (MEM) Alpha Medium containing nucleic acids (Gibco, α⁺ MEM medium) supplemented with 10% fetal bovine serum (FBS, Flow Lab.), penicillin G as antibiotic (50 U/mL) and 50 μg/mL streptomycin, were first inoculated to $1.6 \times 10^6$ cells/30 mL/T80 per 80 cm² T-flask (T80, Nunc) 12 hours prior to gene transfection, after which the medium was replaced with 30 mL of fresh α⁺ MEM medium (containing 10% FBS and antibiotic) 4 hours prior to gene transfection.

On the other hand, plasmids pKDPXA457 and pKDPXA799 Bgl II were respectively dissolved in 240 μL of sterile purified water per 10 μg of plasmid, followed by the addition of an equal amount of Buffer A (0.5 M $CaCl_2$, 0.1 M HEPES) and mixing. After allowing to stand for 10 minutes at room temperature, 480 μL of Buffer B (0.28 M NaCl, 0.05 M HEPES, 0.75 mM $NaH_2PO_4$, 0.75 mM $Na_2HPO_4$) were added to this mixed solution. By allowing to stand for 20 to 30 minutes at room temperature after stirring for several seconds with a Vortex Mixer, a calcium phosphate precipitates were formed that contained the plasmids. Next, 960 μL of the calcium phosphate precipitates containing the plasmids thus obtained were added to CHO dhfr⁻ ($1 \times 10^6$ cells/30 mL/T80) prepared according to the above-mentioned method and allowed to stand for 4 hours.

Next, after washing the cells once with 10 mL of fresh α⁺ MEM medium not containing FBS, 5 mL of a 4:1 mixture of α⁺ MEM medium containing 10% FBS and glycerol were added per T80 flask, and after waiting exactly 1 minute, the mixture was removed by suction. 30 mL of μ⁺ MEM medium containing 10% FBS was again added, followed by culturing at 37° C. in the presence of 5% $CO_2$. Next, after culturing the cells for 4 days, the cells were peeled from the flask with 0.25% trypsin solution (Chiba Kessei). The cells were again inoculated to $1.6 \times 10^6$ cells/30 mL/T80 in an MEM medium not containing nucleic acids (α⁻MEM) into which 10% dialyzed fetal bovine serum ($FBS^d$, Haezleton) had been added.

Next, after culture the cells for 10 days, the following experiment was performed on those cells containing the target plasmids and surviving in the medium (cells containing pKDPXA457 are referred to as CHO/pKDPXA457-α, while those containing pKDPXA799 Bgl II are referred to as CHO/pKDPXA799 Bgl II-α).

In order to perform gene amplification in cells CHO/pKDPXA457-α and CHO perform gene amplification /pKDPXA799 Bgl II-α (pKDPXA457 or pKDPXA799 Bgl II) thus obtained, the above-mentioned cells were cultured in media containing sequentially increasing concentrations of methotrexate (MTX, Sigma) at 30 nM, 100 nM, 300 nM and 1000 nM to obtain cells having various levels of MTX resistance.

Next, those cells that acquired 1000 nM MTX-resistance thus obtained (these cells are referred to as CHO/pKDPXA457-1 and CHO/pKDPXA799 Bgl II-1, respectively) were respectively inoculated to $6 \times 10^6$ cells/30 mL/T80 and cultured at 37° C. for 4 days in the presence of 5% $CO_2$. Next, a portion of the culture was removed from both cultures and the activity of C-terminal α-amidating enzyme was assayed using the synthetic substrate Ac-[$^{125}$I]-Tyr-Phe-Gly (see, Example 1 described later in regard to the definition of the measurement method and units for assay of C-terminal α-amidating enzyme activity). As a result, 1 unit/mL and 310 units/mL of enzyme activity were found to be contained in the culture of CHO/pKDPXA457-1 and CHO/pKDPXA799 Bgl II-1, respectively.

According to the above-mentioned results, since cells transfected pKDPXA799 Bgl II were found to exhibit higher enzyme activity than cells transfected pKDPXA457, cloning was performed by the critical dilution method for the above-mentioned MTX 100 nM-resistant CHO/pKDPXA799 Bgl II cells in order to establish a high C-terminal α-amidating enzyme-producing cell line. Namely, MTX 100 nM-resistant CHO/pKDPXA799 Bgl II cells were inoculated in a 96-well flat bottom plate (Corning) so as to contain on average 3 units, 1.5 units, 0.75 units or 0.375 units/well. These cells were then cultured for 1 week in 100 μL/well of α⁻MEM medium containing 10% FBS.

One week later, 100 μL of α⁻MEM medium were added to 30 wells in which cells had grown to form a single colony as determined by microscopic observation, after which the cells were cultured for an additional week. Two weeks after the cells were inoculated, enzyme activity of the culture supernatant was assayed for these 30 cells. As a result, the cells named CHO/9C were found to exhibit the highest enzyme activity (910 units/mL) among these cells. Next, these CHO/9C cells that demonstrated the highest enzyme activity were further cultured in increasing concentrations of MTX at 0.1, 0.3, 1, 3, 10 and 30 μM to obtain various levels of MTX-resistant cells. After respectively culturing the MTX-resistant cells thus obtained for 4 days under conditions of $1.6 \times 10^6$ cells/30 mL/T80 using α⁻MEM medium containing 10% FBS, the enzyme activity of the culture supernatant was assayed. As a result, MTX 3 μM-resistant line 9C was found to demonstrate the highest enzyme activity (2860 units/mL).

Reference Example 2

Acquisition of 3μ-1S Cells

3μ-1S cells were able to be acquired according to the following method.

First, cloning was performed from the 3 μM MTX-resistant 9C line described in Reference Example 1 using the method described in Reference Example 1. Namely, 3 μM MTX-resistant line 9C cells were inoculated in a 96-well plate (Corning) and cultured for 1 week in 100 μL/well of Minimum Essential Medium (MEM) Alpha Medium not containing nucleic acid (α⁻MEM medium, Gibco) supplemented with 10% dialyzed bovine fetal serum (FBS$^d$).

Moreover, 100 μL/well of α⁻MEM medium was further added, followed by additional culture for 1 week. The resulting high amidating enzyme-producing cells were referred to as 3μ-1 cells. Next, the 3μ-1 cells were suspended by shake culture (culture volume: 60 mL/flask) in F-12CMG2T medium (Ajinomoto) containing 10% FBS$^d$ and 1.0 μM MTX using a siliconized 300 mL volumetric Erlenmeyer flask. Moreover, the serum concentration in the medium was gradually decreased to obtain 3μ-1S cells that were ultimately acclimated to serum-free medium which was the F-12CMG2T medium containing 5 μg/mL each of insulin and transferrin and 1.0 μM MTX.

Reference Example 3

Determination of Optimum Temperature Shift Time in Batch Culturing of 3μ-1S cells The optimum temperature shift time in batch culture of 3μ-1S cells can be determined by this experiment. In addition, the optimum temperature shift time during batch culture can also be determined for other cell lines by performing an experiment similar to this experiment.

Figure 16:
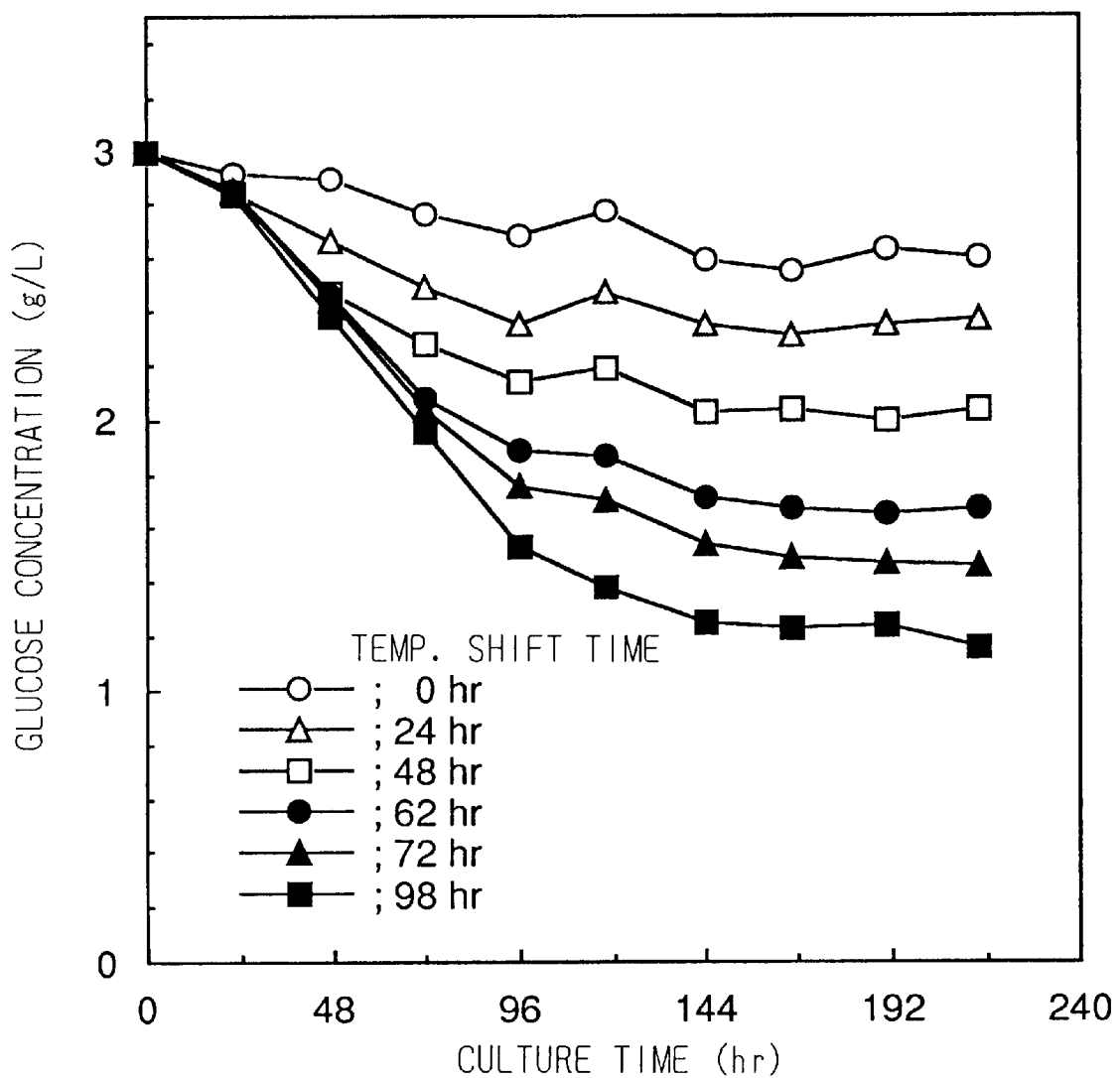
FIG. 16 is a graph showing changes with time elapsing in glucose concentration in the medium during the culture indicated in FIG. 15.

Preculture and an inoculation to a 1 L spinner flask (6) were carried out using methods similar to those of Example 1 to be described later, after which culture was started (the culture volume of each culture vessel was set at 650 mL). The culture temperatures were set at 36° C. for the primary culture temperature and 32° C. for the secondary culture temperature, and temperature shift was performed 0, 24, 48, 62, 72 and 98 hours after inoculation. The reason for setting the primary culturing temperature at 36° C. is that the optimum growth temperature of 3μ-1S cells in Example 1 to be described later was 36° C. pH was controlled at 7.2 for all culture vessels. The stirring rate of the spinner flask was adjusted to 100 rpm. Oxygen was supplied by 100 mL/min of continuously gassing with air through a Teflon membrane. In these culture conditions, we confirmed that DO was kept above 60% air saturation. Samples were taken every 24 hours on which were performed a cell count, assay of AE activity and measurement of glucose. Those results are shown in FIGS. 15 to 17.

FIGS. 15 (A) through (F) indicate the changes in cell density in the culture at the time of each temperature shift. The arrows in the drawings indicate the times of each temperature shift, the black dots indicate total cell density, and the white dots indicate viable cell density. In the case where temperature was shifted during the logarithmic growth phase (24 to 72 hours of culturing), cell growth stopped within 24 hours after the shift, after which cell density gradually decreased (FIGS. 15 (B)–(E)). In the case where temperature was shifted during the steady phase (98 hours of culturing), the decrease of viability in the latter half of culture was remarkable, with an extremely large amount of debris (dead cell fragments) being observed in the culture liquid (FIG. 15 (F)). In addition, glucose consumption decreased after the temperature shift in the same manner as cell growth (FIG. 16).

Figure 17A:
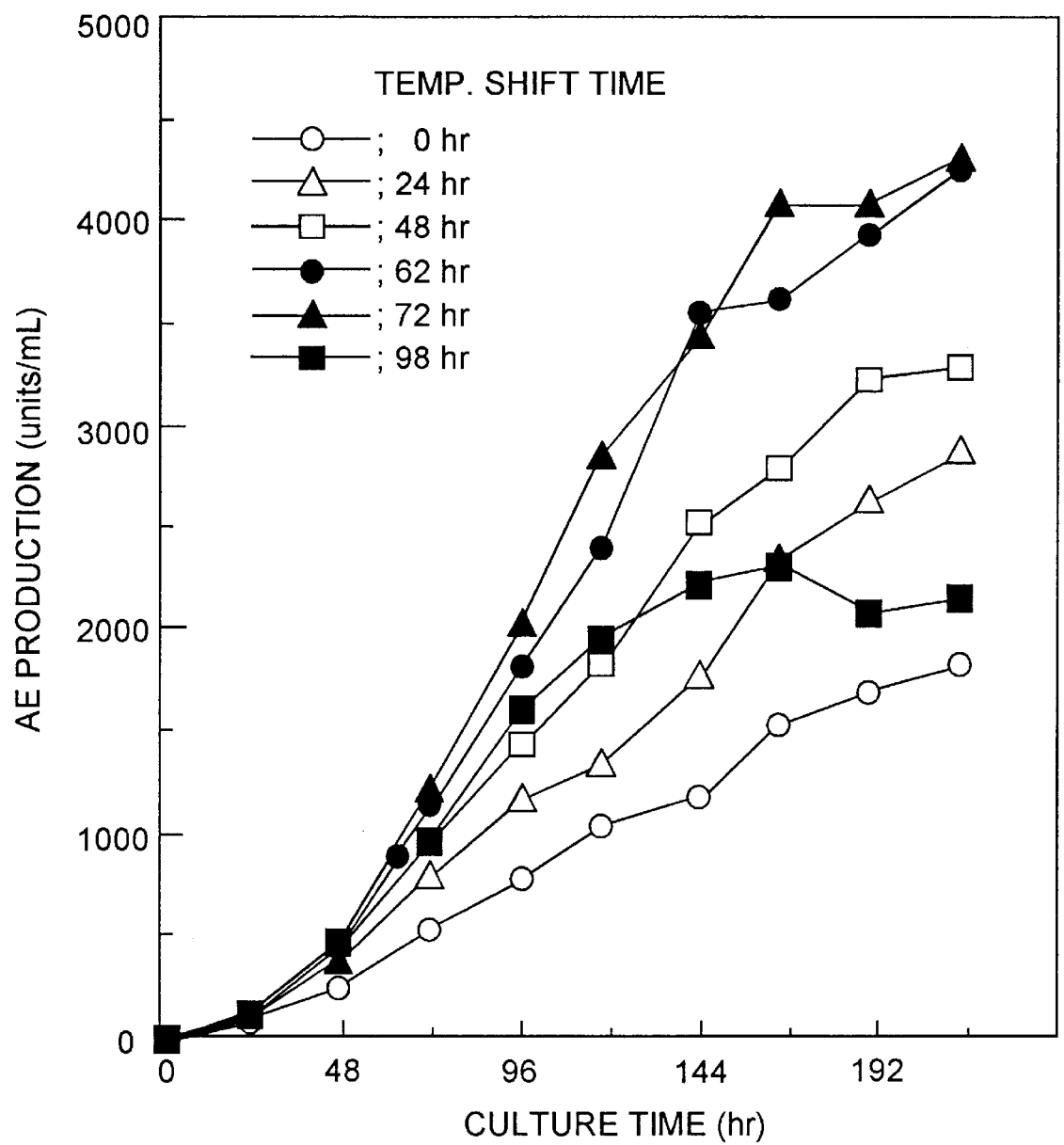
FIG. 17 shows the AE production (accumulated amount) in the culture indicated in FIG. 15. (A) is a graph indicating changes with time elapsing in AE production with culture time plotted on the horizontal axis. (B) is a graph showing the effect of temperature shifting time on AE production at various culture times, with temperature shift time plotted on the horizontal axis.
Figure 17B:
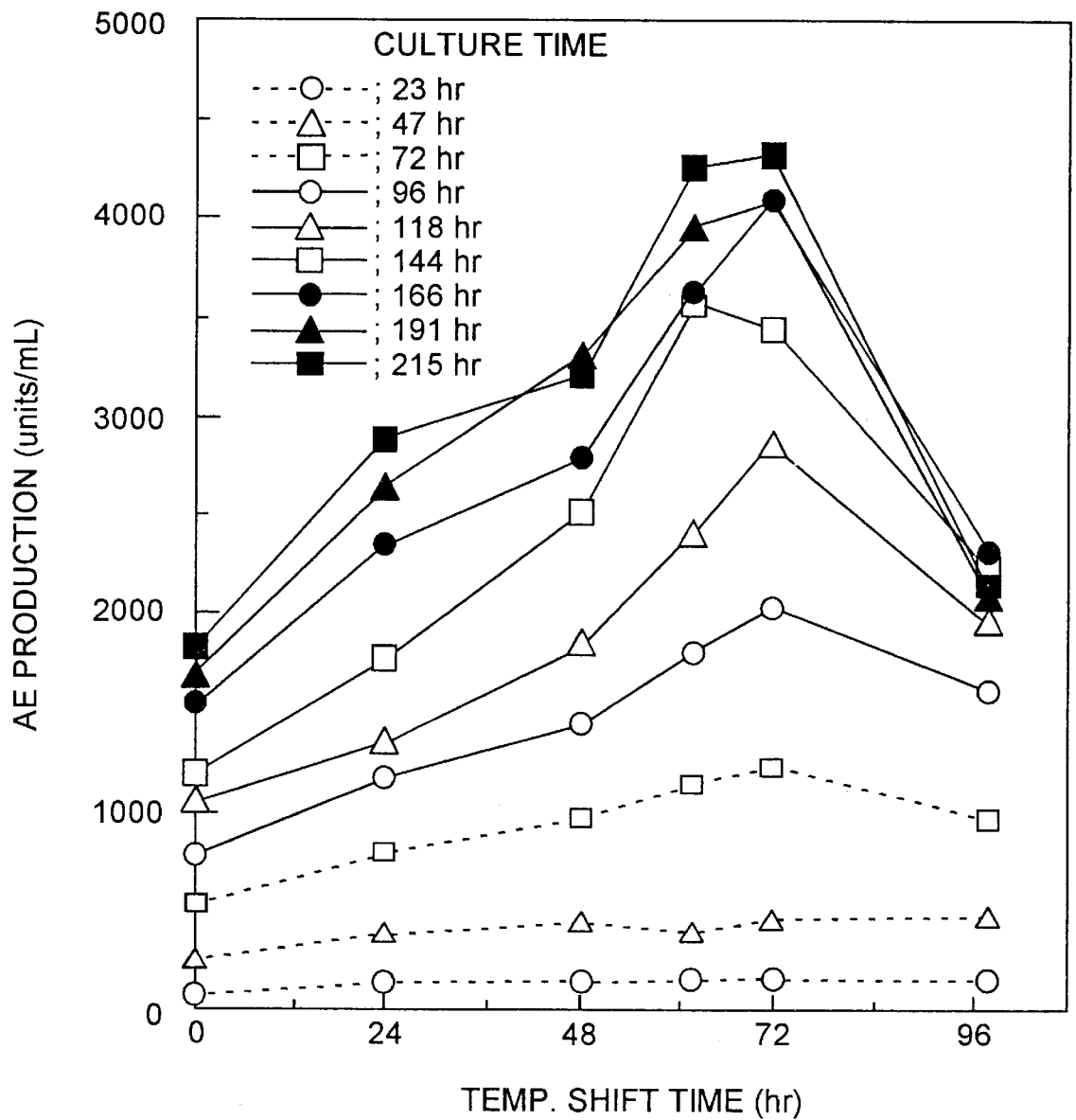

The effect of temperature shift time on AE production is shown in FIGS. 17 (A) and (B). In (A), culture time is plotted on the horizontal axis, and in (B), temperature shift time is plotted on the horizontal axis. The amount of AE produced increased in the case where temperature was shifted during the logarithmic growth phase, and increased the highest level as a result of temperature shift at 62 to 72 hours after inoculation, reaching a level of 4300 units/mL after 9 days of culture (215 hours). On the other hand, in the case of a temperature shift during the steady phase (98 hours of culture), AE production fell to a low level (2200 units/mL). Here, although the amount of AE produced in this experiment is low overall in comparison with the results in Example 1, this difference is due to a difference to the increase in the number of generations of 3μ-1S cells.

The increase in AE production caused by a temperature shift in batch culture is believed to be intimately related to cell growth at the primary culture temperature (36°) (ensuring an adequate number of cells) and the consumption of medium components or accumulation of harmful metabolites accompanying that growth. Thus, according to the results obtained from this experiment, the optimum time for temperature shift is the time at which the amount of AE production has sufficiently increased and consumption of medium components or accumulation of harmful metabolites is at as low a level as possible. Namely, the optimum time is considered to be 62 hours after the start of culturing.

However, in the case of increasing the scale of the experiment for large-volume production, since it is possible that the cell growth rate may be different from the case of culture on a scale of only 1 liter, the temperature shift time cannot simply be determined from the culture time obtained when conducting the experiment on a 1 liter scale. From the viewpoint of consumption of medium components or accumulation of harmful metabolites, it is considered preferable to use cell growth as an indicator of the temperature shift time in the case of batch culturing. Thus, in this experiment, since the cell density after 62 hours of culturing was $5 \times 10^5$ cells/mL, and the cell density attained at 36° C. was $8.5 \times 10^5$ cells/mL, the optimum temperature shift time in batch culture of $3\mu$-1S cells is estimated to be the time at which 59% of the cell density that can be achieved at the primary incubation temperature (36° C.) is reached.

Example 1
Effect of Incubation temperature on $3\mu$-1S Cells in the form of AE-Producing Suspended Cells $3\mu$-1S cells subcultured in 300 mL volumetric Erlenmeyer flasks were inoculated into a 3 liter spinner flask at $2 \times 10^5$ cells/mL and culture volume of 1500 mL, followed by culture for 3 days at 37° C. The medium used here was a serum-free medium in which insulin and transferrin were added to concentrations of 5 $\mu$g/mL each in F-12CMG2T medium (Ajinomoto) (to be simply referred to as medium). After completion of preculture, the $3\mu$-1S cells were recovered by centrifugal separation (1000 rpm, 5 minutes) and suspended in fresh medium.

This cell suspension was inoculated to a cell density of $2 \times 10^5$ cells/mL and culture volume of 750 mL in six 1 liter spinner flasks that allowed control of temperature, dissolved oxygen (DO) and pH, after which culture was started. Here, the culture temperatures were controlled to 30, 32, 33.5, 35, 36 and 37° C. for each of the culture vessels. DO was kept above 60% air saturation by 100 mL/min of continuously gassing with air as described previously. pH was controlled to 7.2 for all culture vessels. In addition, the stirring rate of the spinner flasks was adjusted to 100 rpm. The cells were cultured for 5 days.

Samples of culture were taken every 24 hours to determine the total and viable cell density and glucose concentration in the medium. The total and viable cell density were daily determined by trypan blue dye exclusion method in a hemacytometer after treatment with trypsin. The glucose concentration in the culture supernatant was also measured daily by Glucose analyzer ST-1 (Oriental electric). All samples including cell suspension, cells and supernatant were stored at −20° C. until required.

Assay of AE activity was performed using a synthetic substrate Ac-[$^{125}$I]-Tyr-Phe-Gly (see, Biochem. Biophys. Res. Commun., Vol. 137, pp.984–991, 1986 and Japanese Unexamined Patent Publication No. 1-104168). The enzymatic activity of 1 unit is defined as the amount of activity that amidates 50% of 1 pmole of substrate in 1 hour at 37° C. under standard reaction conditions. Amino acid analysis was performed using the Model L-8500 Amino Acid Analyzer (Hitachi). In addition, samples of culture (cell suspension) and culture supernatant for measurement of cell lysis ratio, samples of culture supernatant for SDS-PAGE and Western blotting, and samples of cells for Southern and Northern blot analysis were taken on days 3 and 5 of culture and stored frozen at −20° C.

(1) Effect of Culturing Temperature on Cell Growth

The effect of culturing temperature on cell growth is shown in FIG. 1. The black dots in the graph indicate total cell density, and the white dots indicate viable cell density. Cell growth was the most favorable at 360° C., and was inhibited accompanying a decrease in incubation temperature below 36° C. Below 32° C., it was completely suppressed. On the other hand, cell viability tended to decrease as culture temperature increased.

(2) Effect of Culture Temperature on AE Production and Productivity

Figure 2:
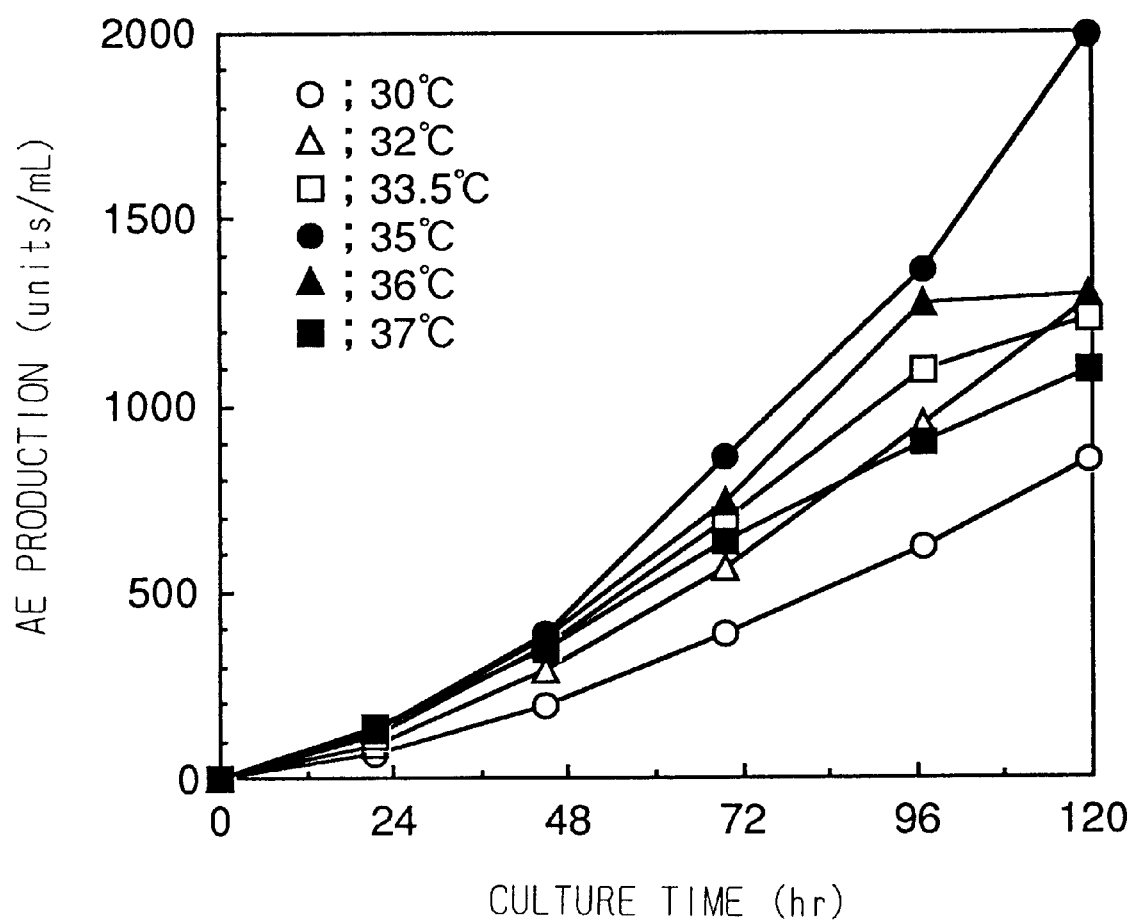
FIG. 2 is a graph that shows changes with time elapsing in the production (accumulated amount) of amidating enzyme (AE) by 3μ-1S cells at various culture temperatures.

AE production is shown in FIG. 2. AE production exhibited a maximum at 35° C., reaching a level of 2000 units/mL after 5 days of culture. At temperatures of higher and lower than 35° C., AE production decreased as culture temperature increased or decreased.

Figure 3:
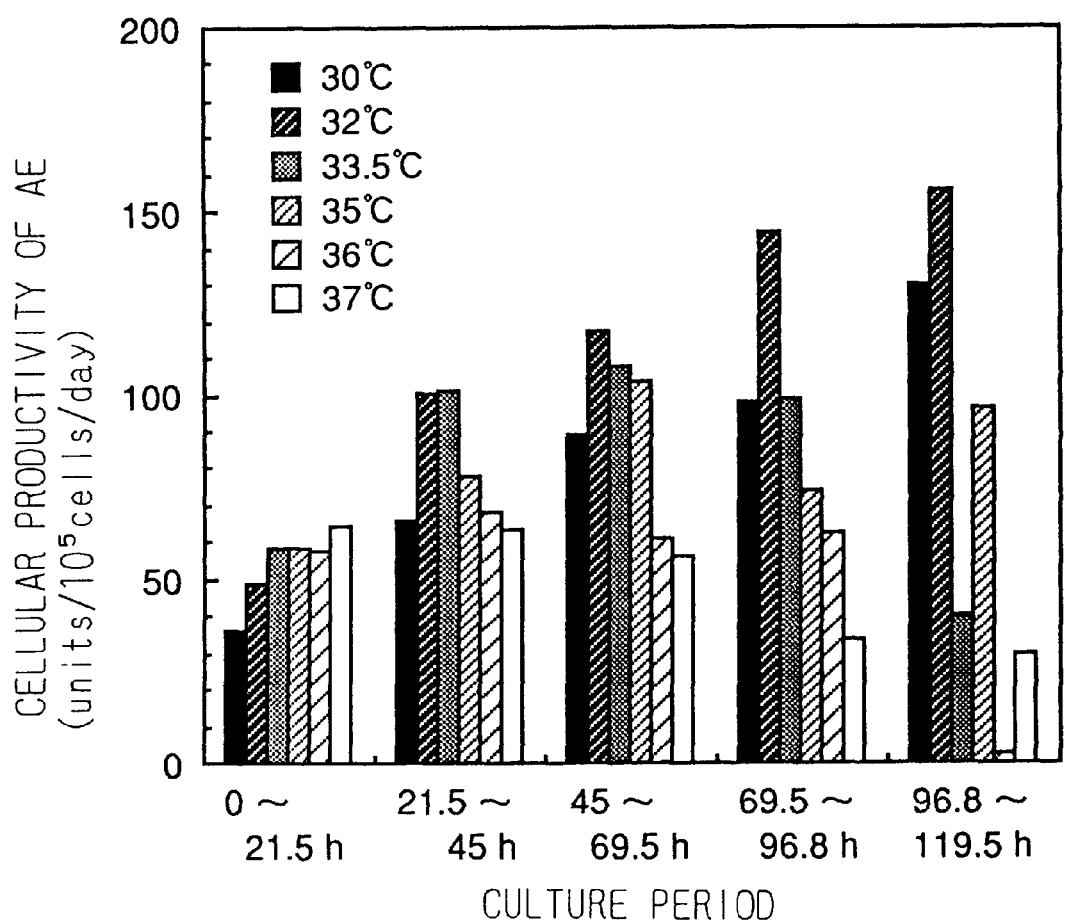
FIG. 3 is a graph that shows changes with time elapsing in cellular productivity of AE at various culture temperatures. The productivity was calculated from the results shown in FIGS. 1 and 2.

AE productivity per cell was calculated from FIGS. 1 and 2. Those results are shown in FIG. 3. At 30° C. and 32° C., productivity increased as culture progressed, with the highest productivity being demonstrated at 32° C. On the other hand, at culture temperatures of 33.5° C. and above, the increase in productivity lowered as culture progressed, with productivity itself eventually tending to decrease. This trend become more prominent as culture temperature was increased.

(3) Genetic Analysis

Qualitative and quantitative changes in AE-DNA and mRNA caused by culturing temperature were studied by Southern and Northern blotting, respectively.

Southern blot analysis: Genomic DNA was isolated from the cells cultured at various temperature by using DNA isolation kit (Bio 101). The DNA sample was digested with a restriction enzyme (EcoRI) followed by agarose gel electrophoresis at 1 $\mu$g/lane. Following electrophoresis, DNA in the gel was denatured with alkali and transferred to a nylon membrane (Hybond-N+, Amersham) under a vacuum.

After cross-linking by UV radiation, pre-hybridization was performed for 2 hours at 42° C. [Pre-hybridization solution: 5xSSC (20xSSC; 3 M NaCl, 0.3 M trisodium citrate), 5x Denhardt's sol. (100x Denhardt's sol.; 2% (w/v) BSA (bovine serum albumin), 2% (w/v) Ficoll™, 2% (w/v) PVP (polyvinylpyrrolidone)), 0.5% (w/v) SDS, 50% (v/v) formamide, 100 $\mu$g/mL herring sperm DNA (fragmentated and heat-denatured)]. The AE plasmid, pKD799BglII (Animal Cell Technology: Basic & Applied Aspects, Vol. 5, 493–499 (1993) and Japanese Unexamined Patent Publication No. 2-190193) was digested with EcoRI to obtain a fragment of AE DNA.

Using this fragment as the template, a $^{32}$p-labelled AE probe, synthesized by using Megaprime™ DNA labelling systems, was added to the pre-hybridization solution to a concentration of $1 \times 10^6$ cpm/mL to obtain the hybridization solution. The pre-hybridization solution used for pre-hybridization was replaced with the hybridization solution, after which hybridization was performed overnight (16 hours) at 42° C. After stringency washes of the membrane, the blots were analyzed by imaging plate (IP)-autoradiography using Bio-imaging analyzer BAS2000II (Fuji Photo Film).

Northern blot analysis: Total RNA was isolated from the cells cultured at various temperature by using TRIzol™ reagent (Gibco BRL). Agarose gel electrophoresis was performed on the RNA sample in the presence of formalin at 20

μg/lane. After electrophoresis, the RNA in the gel was transferred to a nylon membrane under a vacuum. After cross-linking by UV radiation, pre-hybridization was performed for 2 hours at 42° C. The previously mentioned $^{32}$P-labelled AE probe was added to the pre-hybridization solution at a concentration of $5\times10^5$ cpm/mL to obtain the hybridization solution.

The pre-hybridization solution used for pre-hybridization was replaced with the hybridization solution and hybridization was performed overnight (16 hours) at 42° C. After stringency washes of the membrane, the blots were analyzed by imaging plate (IP)-autoradiography using Bio-imaging analyzer BAS2000II (Fuji Photo Film). Subsequently, the AE probe hybridized was removed by boiling the membrane with 0.5% (w/v) SDS solution for 30 minutes, in order to re-hybridize to a $^{32}$P-labeled β-actin probe. The probe was synthesized using a human β-actin cDNA (Clontech) as the template by using Megaprime™ DNA labeling systems. Hybridization and analysis were performed in the same manner.

Figure 4:
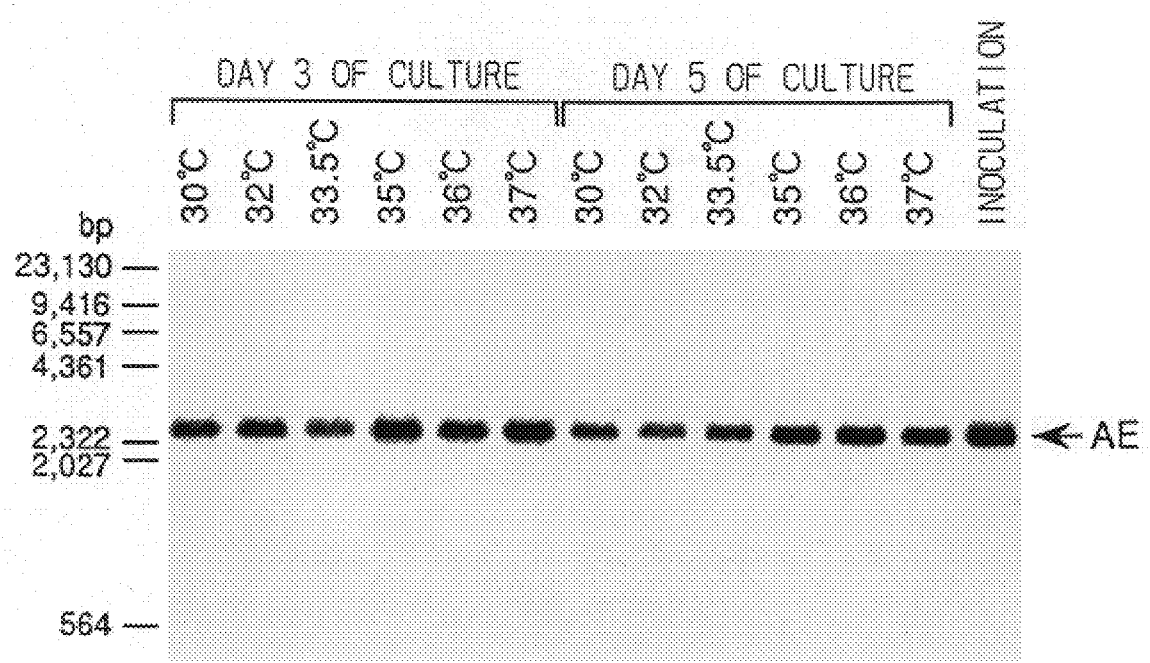
FIG. 4 shows the result of Southern blot hybridization. AE-DNA in 3μ-1S cells at the indicated times of culturing and at various incubation temperatures were detected.
Figure 5:
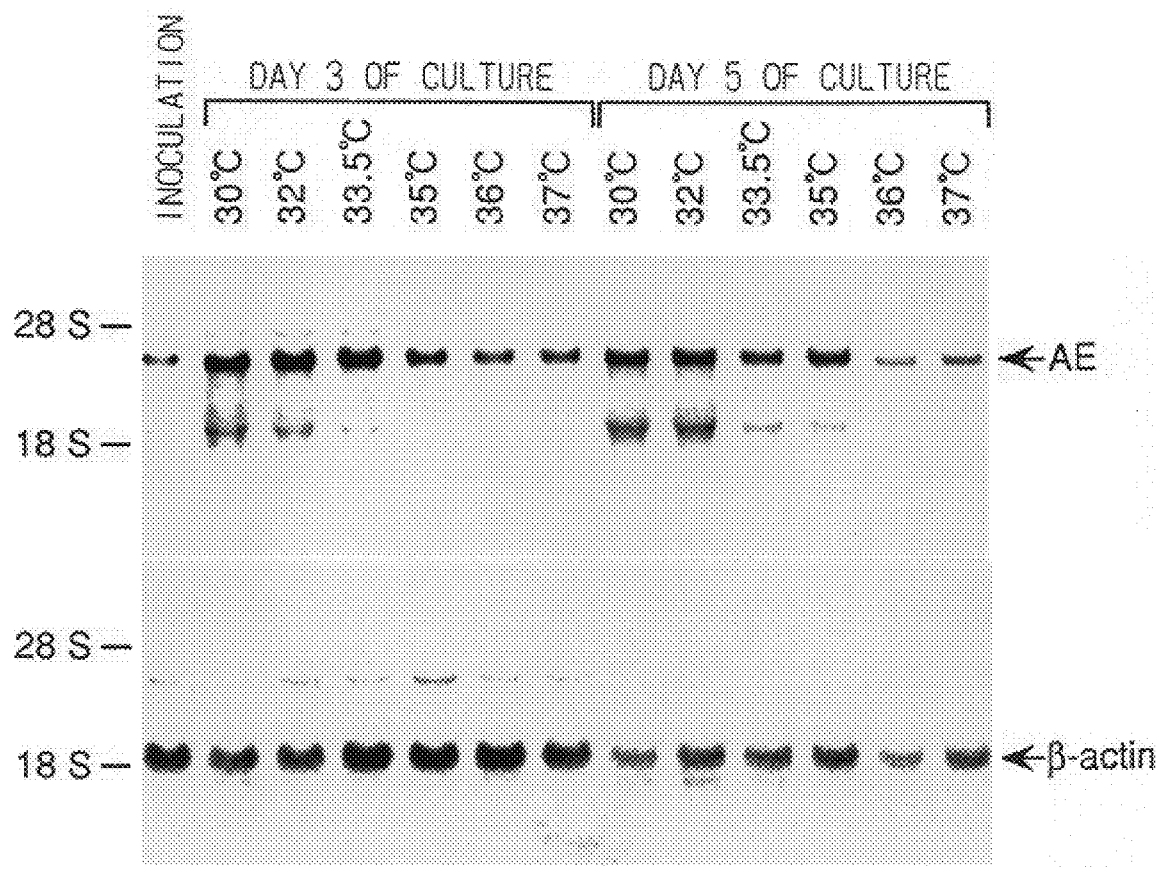
FIG. 5 shows the result of Northern blot hybridization. AE-mRNA, contained in 3μ-1S cells at the indicated times of culturing and at various incubation temperatures, along with β-actin-mRNA, used as an internal standard were detected.

The results of Southern blot hybridization are shown in FIG. 4. AE-DNA demonstrated the same molecular size for all samples (2,351 bp), and culture temperature was not observed to cause any qualitative changes. In addition, there were also no significant quantitative changes observed. In contrast, the amount of AE-mRNA was observed to demonstrate a remarkable increase as culture temperature decreased (FIG. 5). Here, in addition to the main band of AE-mRNA, another band was observed in the vicinity of 18S-rRNA. The origin of this band, however, remains unknown. However, since the main band of AE-mRNA exhibits the same molecular size, AE-mRNA in the main band can be said to have not undergone any qualitative changes. In addition, since quantitative changes in β-actin-mRNA caused by incubation temperature were not observed, β-actin-mRNA was confirmed to be able to use as an internal control of this analysis.

Figure 6:
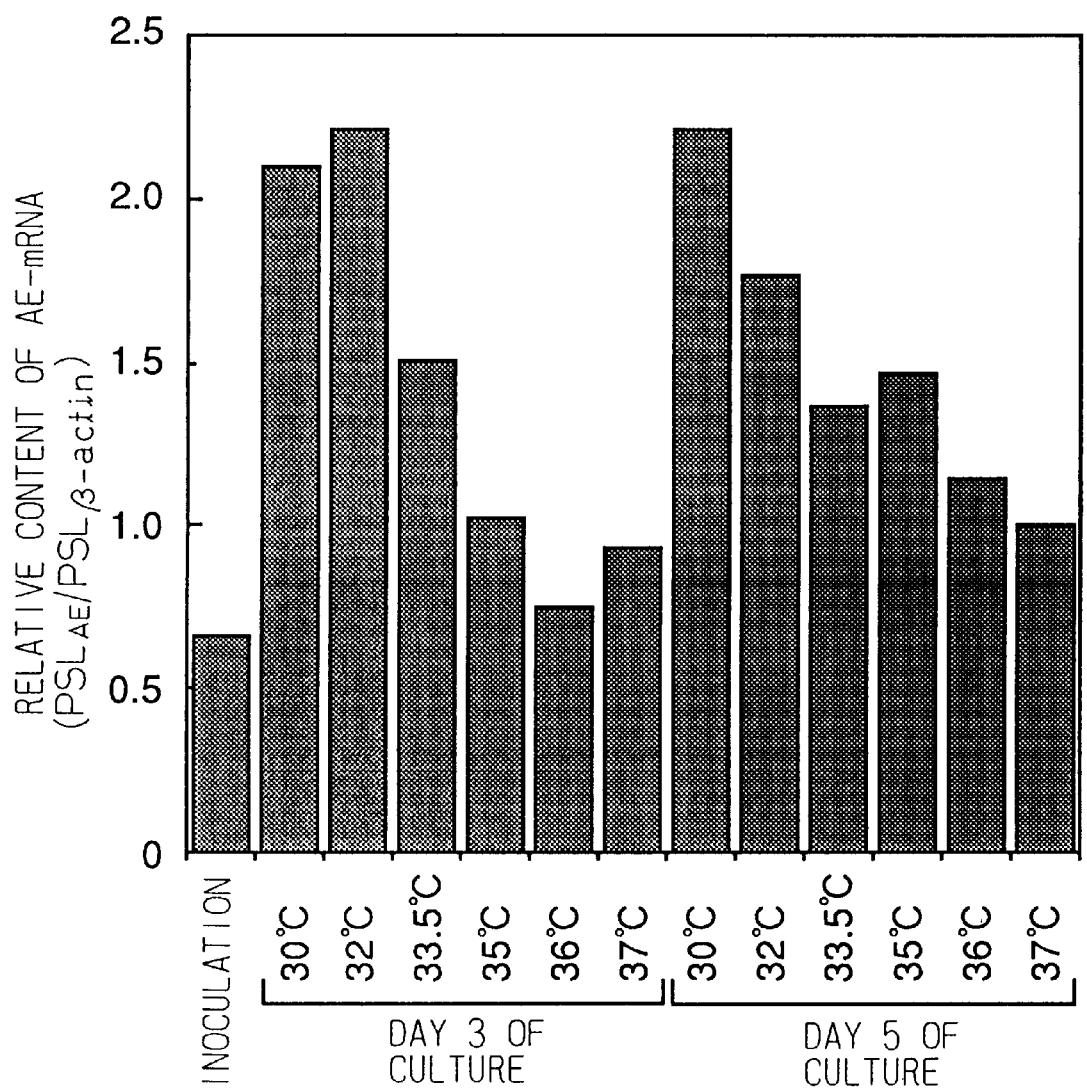
FIG. 6 shows the relative content of AE-mRNA in 3μ-1S cells at the indicated times of inoculation and at various incubation temperatures. The relative content of AE-mRNA was calculated as the ratio of the PSL (photo-stimulated luminescence) value of AE-mRNA band to the PSL value of the β-actin-mRNA band obtained in FIG. 5.

In order to more accurately determine quantitative changes in AE-mRNA, the signal of each main band was quantitated as photo-stimulated luminescence (PSL) value, and each the relative content of AE-mRNA was obtained as the ratio of the PSL value of AE-mRNA main band to that of β-actin-mRNA main band. This result is shown in FIG. 6.

The relative content of AE-mRNA increased as culture temperature decreased, reaching levels at 30° C. and 32° C. that were 1.8 to 2.4 times greater than the content at 37° C. Thus, the increase in the AE-mRNA content is considered to be an important factor of increases in AE productivity resulting from decreases in culture temperature. However, since AE productivity per cell reached levels at 30° C. and 32° C. that were 4.3 to 5.3 times greater than the level at 37° C. on day 5 of culturing (FIG. 3), culture temperature is thought to have an effect both in the AE-mRNA translation process or AE secretion process.

(4) Effect of Culture Temperature on Medium Component Consumption

Consumption of glucose and amino acids was studied as indicators of medium consumption. Glucose consumption rate and amino acid consumption rate were calculated in terms of the mean value for 5 days of culture from glucose concentration or various amino acid concentrations in the culture supernatant and viable cell density (FIG. 1). Those results are respectively shown in FIG. 7 and Table 1.

TABLE 1

| Amino Acid | Consumption rate ($\mu$g/$10^5$ cells/day) | | |
|---|---|---|---|
| | 37° | 35° C. | 32° C. |
| Asp | 0.67 | 0.73 | 0.86 |
| Thr, Gln | 10.27 | 9.04 | 7.66 |
| Ser, Asn | 3.80 | 3.26 | 2.84 |
| Glu | −1.67 | −1.22 | −1.28 |
| Cysteine | 2.21 | 2.07 | 1.42 |
| Gly | −1.36 | −1.13 | −1.38 |
| Ala | −3.86 | −3.05 | −1.78 |
| Val | 0.65 | 0.64 | 0.48 |
| Cysteine | 0.37 | 0.15 | 0.07 |
| Met | 0.29 | 0.29 | 0.21 |
| Ile | 1.13 | 1.04 | 1.24 |
| Leu | 1.26 | 1.18 | 1.18 |
| Tyr | 0.40 | 0.40 | 0.25 |
| Phe | 0.48 | 0.47 | 0.31 |
| Lys | 0.77 | 0.75 | 0.41 |
| His | 0.39 | 0.23 | 0.16 |
| Trp | 0.15 | 0.16 | 0.09 |
| Arg | −0.46 | −0.57 | −0.64 |
| Pro | 0.16 | 0.13 | 0.00 |

Figure 7:
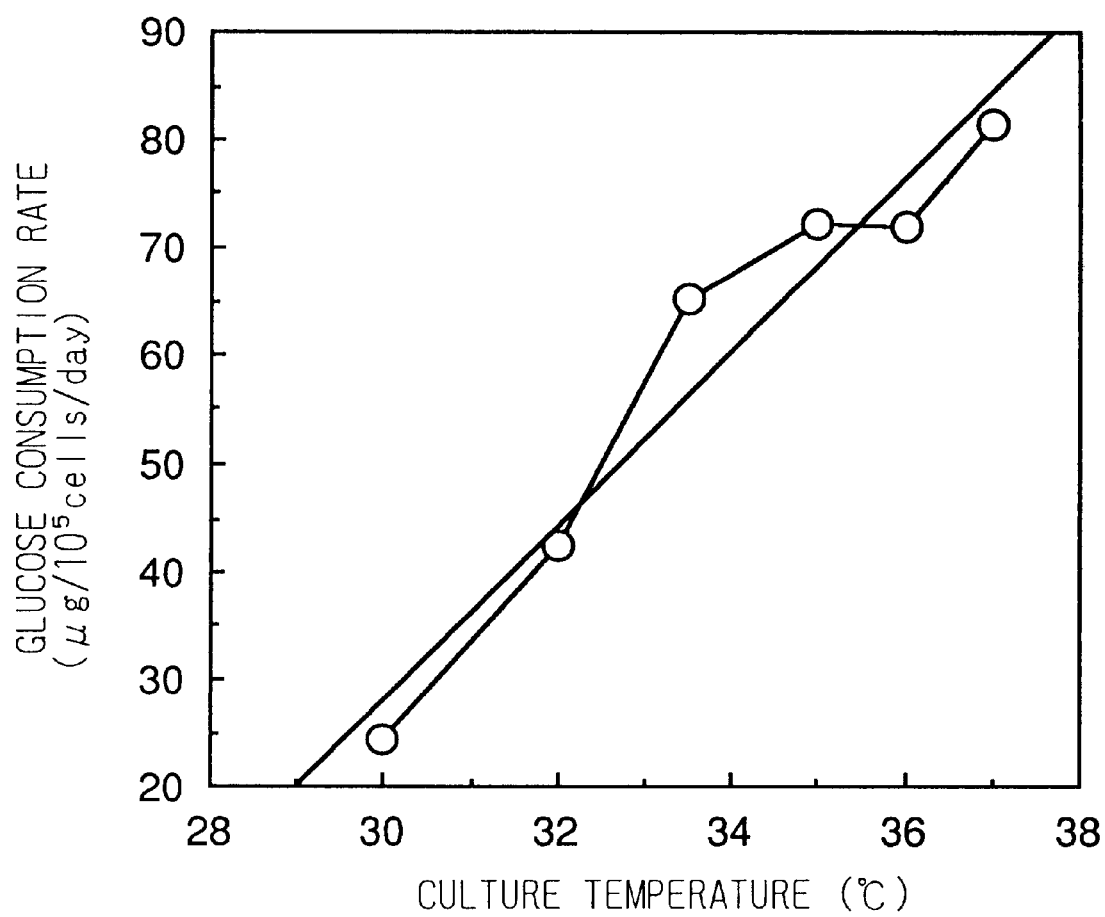
FIG. 7 is a graph showing the effect of culture temperature on the rate of glucose consumption per $10^5$ 3μ-1S cells.

The rate of glucose consumption decreased with decreasing culture temperature, from 80 $\mu$g/$10^5$ cells/day at 37° C. to 24 $\mu$g/$10^5$ cells/day at 30° C. (FIG. 7). In addition, although the rate of amino acid consumption increased for Asp and Ala as incubation temperature decreased (although production rate decreased for Ala), there were no changes in the consumption rates of Glu, Gly, Met, Ile and Leu, while that for all other amino acids decreased (Table 1). On the basis of these results, it was clear that consumption of the majority of medium components decreases as culturing temperature decreases. This means that low temperature culture enables substance production to be performed while requiring only a small amount of nutrient components, thus indicating that this type of culturing can contribute to reduction of medium costs.

(5) Effect of Culturing Temperature on Ratio of Lysed Cells

Figure 8:
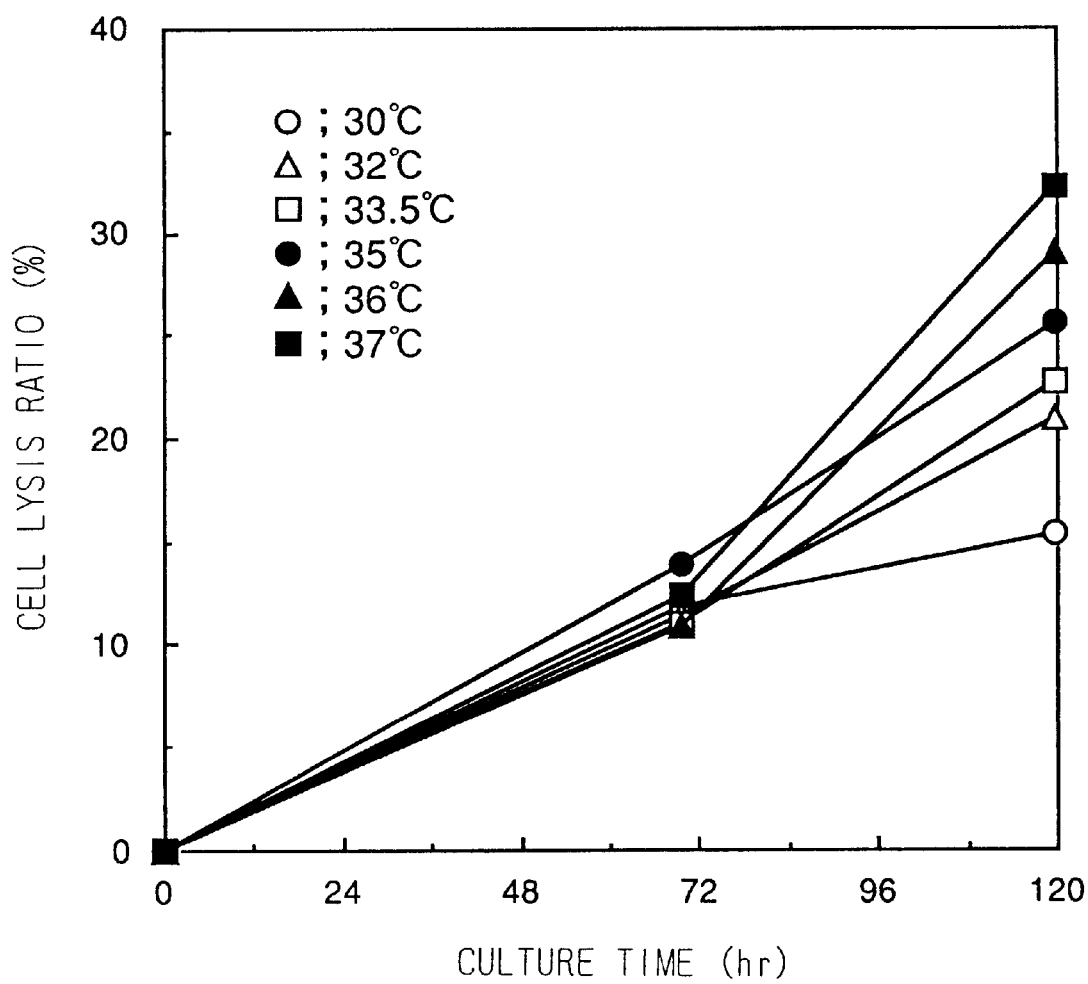
FIG. 8 is a graph showing changes with time elapsing in cell lysis ratio at various culture temperatures. The ratio was calculated from the activities of lactate dehydrogenase (LDH) in the culture supernatant and in the whole culture (cell suspension).

Lactate dehydrogenase (LDH) activity in culture liquid and culture supernatant on days 3 and 5 of culture was assayed, and ratio of lysed cells was calculated as the ratio of the latter to the former (%). Those results are shown in FIG. 8.

Through 72 hours of culturing, there were no significant differences in ratio of lysed cells accompanying changes in culture temperature (11 to 14%). However, after 120 hours of culturing, the ratio of lysed cells increased as culturing temperature increased (30° C.: 15%, 37° C.: 32%). This finding indicates that lowering culture temperature not only maintains the cells in good condition thereby enabling culture to be prolonged for a long time, but also inhibits contamination of the medium by contaminating proteins originating in cells containing proteases.

(6) Analysis of AE protein by SDS-PAGE and Western Blotting

The effect of culture temperature on the purity of AE protein during culturing was examined by SDS-PAGE. Aliquots of each supernatant on day 5 of culture, corresponding to 45 units of AE activity, were applied to 10% polyacrylamide gel containing SDS (SDS-PAGE mini, Tefco). Electrophoresis was performed at a constant current of 25 mA, and the gel was stained with CBB. Furthermore, Wide-Range SDS-PAGE Protein Standards (Tefco) were used for the molecular weight markers. This result is shown in FIG. 9.

The samples in each lane, starting with line 1 in order, consisted of culture supernatant at 30° C., 32° C., 33.5° C., 35° C., 36° C. and 37° C. In addition, the arrows on the left side of the figure indicate the locations of the molecular weight markers, while the arrows on the right side (81 and 75 kDa) indicate AE. Furthermore, the two bands directly below AE are bands representing transferrin that was added to the medium. Contaminating proteins contained in the culture supernatant decreased remarkably as culture temperature decreased. This finding indicates that culture at low temperatures is advantageous in the purification process of AE as well. The decrease in contaminating proteins resulting from culturing at low temperature is considered to be the result of slowing of metabolic turnover accompanying reduced consumption of medium (FIG. 7, Table 1), and the decrease in the ratio of lysed cells (FIG. 8).

Next, the effect of culture temperature on AE protein during culture was examined by Western blotting. Aliquots of each supernatant on day 5 of culture, corresponding to 45 units of AE activity, were applied to 10% polyacrylamide gel containing SDS (SDS-PAGE mini, Tefco). Electrophoresis was performed at a current of 25 mA. After the electrophoresis, the protein in the gel was electro-transferred to a PVDF (polyvinylidene fluoride) membrane (Millipore). Transfer was performed for 30 minutes at a constant current of 3 mA/cm$^2$. Following completion of transfer, the PVDF membrane was blocked with 3% gelatin and 0.1% Tween 20-PBS, and treated with biotinized rabbit anti-AE polyclonal antibody (IgG fraction).

After wash with 0.1% Tween 20-PBS, the membrane was treated with horseradish peroxidase avidin conjugate (horseradish peroxidase avidin D, Vector). After again washing with 0.1% Tween 20-PBS, immunoreactive bands were visualized using POD immunostain set (Wako Pure Chemical Industries). Furthermore, SeeBlue™ Pre-Stained Standards (Novex) were used for the molecular weight markers. This result is shown in FIG. 10.

Similar to FIG. 9, the samples in each lane, starting with line 1 in the order, consisted of culture supernatant at 30° C., 32° C., 33.5° C., 35° C., 36° C. and 37° C. In addition, the arrows on the left side of the figure indicate the locations of the molecular weight markers, while the arrows on the right side (81 and 75 kDa) indicate AE. The differences in molecular weight of the AE protein would be due to differences in sugar chain modification. Since the molecular weight of AE protein in all lanes was constant and since there were no changes in the ratio of intensities of both bands (81 and 75 kDa), AE protein was shown to have not undergone any qualitative (molecular weight and sugar chain modification) changes due to culture temperature.

Example 2
Application of Low-Temperature Culture to Batch Culturing

In the case of performing culture below 37° C. according to Example 1, although cell growth is inhibited, it was shown that a high cell viability is maintained, cellular productivity of AE increases, consumption of medium components (glucose, almost amino acids) decreases, and impurity-proteins in the cultured medium decreases. These phenomena indicate that by lowering culture temperature after a sufficient number of cells have been obtained, it is possible to achieve a significant increase in the efficiency of the production of desired substance by animal cell culture. This experiment was conducted to examine the application of this low-temperature culture to batch culture.

3µ-1S cells, subcultured in 300 mL Erlenmeyer flasks, were precultured for 3 days at 37° C. after inoculating into a 3 liter spinner flask to a cell density of $2 \times 10^5$ cells/mL and culture volume of 1500 mL. The previously mentioned serum-free medium was used for the culture medium. Following completion of preculturing, the 3 µ-1S cells were collected by centrifugation (1000 rpm, 5 minutes), and suspended in fresh medium.

Figure 11A:
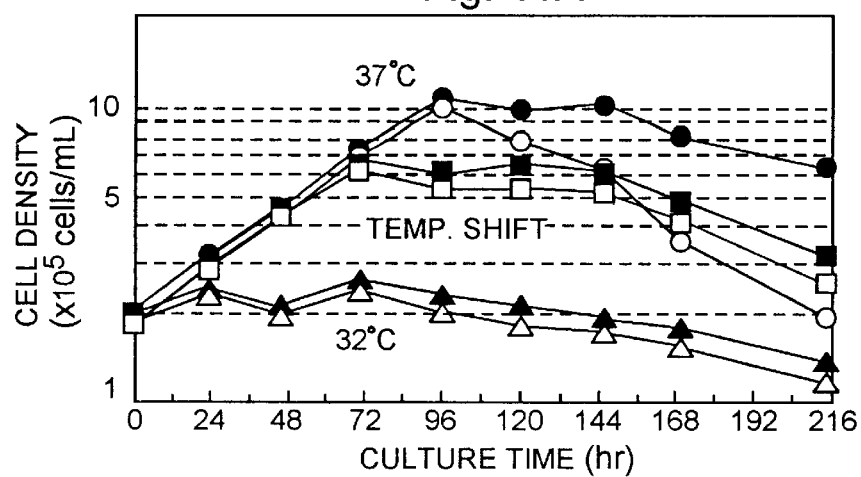
In FIG. 11(A), the white circles, white triangles and white squares indicate viable cell density, while the black circles, black triangles and black squares indicate total cell density.

This cell suspension was then inoculated into a three 1 liter spinner flasks that enabled control of temperature, dissolved oxygen (DO) and pH to a cell density of $2 \times 10^5$ cells/mL and culture volume of 650 mL, after which culture was started. Culture vessels 1 and 2 were cultured at 37° C. and 32° C., respectively, throughout the culture period. Culture vessel 3 was first incubated at 37° C., after which the temperature was shifted from 37° C. to 32° C. after 48 hours of culture and maintained at that temperature for the duration of the culture period. DO was kept above 60% air saturation by 100 mL/min of continuously gassing with air as described previously. pH was controlled to 7.2 for all culture vessels. In addition, the stirring rate of the spinner flasks was adjusted to 100 rpm. Those results are shown in FIG. 11.

The white dots and black dots in the graphs indicate results at a culture temperature of 37° C., the white and black triangles results at 32° C., and the white and black squares results of culture when using a temperature shift. In addition, the white circles, white triangles and white squares in FIG. 11(A) indicate viable cell density, while the black circles, black triangles and black squares indicate total cell density.

During culture at 37° C., the cells demonstrated logarithmic growth while maintaining a high cell viability (92% and above) through day 4 of culturing. Although the cell count reached roughly $1 \times 10^6$ cells/mL, cell growth then stopped, exhibiting a remarkable decrease in viability (31% on day 9 of culturing). In addition, during culture at 32° C., although cell density tended to decrease slightly, viability remained at 85% or more throughout the entire incubation period.

On the other hand, during culture in which temperature was shifted, cell growth nearly equal to that at 37° C. was exhibited through 24 hours after the temperature shift, with cell density reaching $6.5 \times 10^5$ cells/mL. Cell growth stop at 24 to 48 hours after temperature shift. Although a decrease in cell density was later observed, the viability was maintained at 80% or above. On the basis of the above findings, it was shown that cell viability is maintained at a high level and culture can be conducted for a long time by using a lower culture temperature (32° C).

Figure 11B:
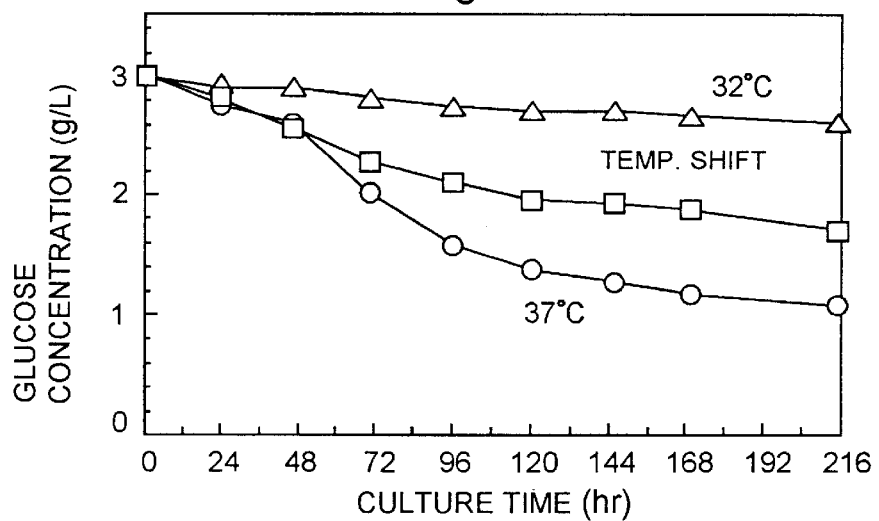
FIG. 11 indicates the effects of a temperature shift from 37° C. to 32° C. during batch culture of 3μ-1S cells. (A) shows changes with time elapsing in cell density, (B) shows changes with time elapsing in glucose concentration in the medium, and (C) shows changes with time elapsing in AE production (accumulated amount). In addition, the white and black circles in the drawing indicate results at 37° C., the white and black triangles those at 32° C., and the white and black squares the results of culturing using a temperature shift.

FIG. 11(B) shows glucose concentration remaining in the medium. It can be understood from this graph that as a result of shifting the temperature from 37° C. to 32° C., glucose consumption decreases in the same manner as culturing at 32° C. Furthermore, although glucose consumption decreases starting at 96 hours of culturing even when culturing at 37° C., this is considered to be the result of a decrease in activity of the cells themselves due to a remarkable decrease in viable cell density. Thus, this is considered to be essentially different from the decrease in glucose consumption brought about by lowering culturing temperature.

Figure 11C:
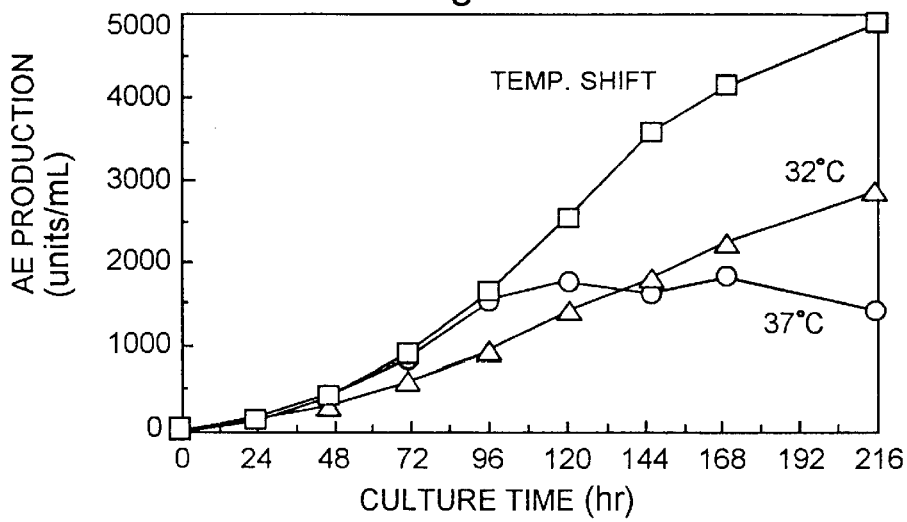
Figure 12:
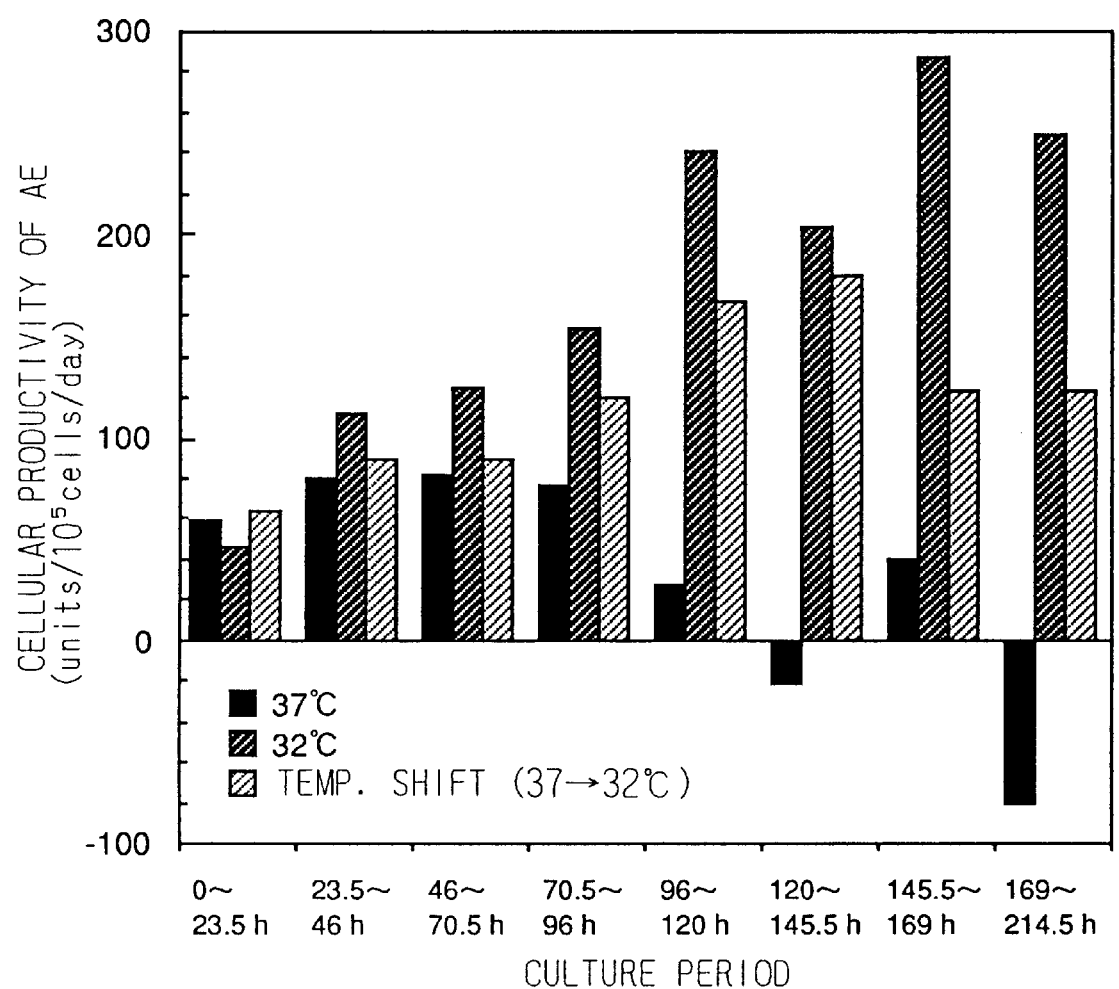
FIG. 12 is a graph showing the changes with time elapsing in cellular productivity of AE, calculated from the results shown in FIGS. 11(A) and (C).

FIG. 11(C) indicates AE production. In the case of culture at 37° C., AE production was only 1800 units/mL. In contrast, in the case of using a temperature shift, AE production reached 5000 units/mL on day 9 of culture, and continued to demonstrate an increasing trend. In the case of culture at 32° C., AE production reached 2900 units/mL after 9 days of culture. In addition, as shown in FIG. 12, in contrast to cellular productivity decreasing starting on day 3 of culturing at 37° C., falling to nearly 0 units/$10^5$ cells/day on day 5 and beyond, in the case of culturing at 32° C., productivity tended to increase as culturing progressed (maximum value: 280 units/$10^5$ cells/day).

Cellular productivity in the case of a temperature shift exhibited lower values in comparison with culture at 32° C. However, cellular productivity increased during the period from 48 to 96 hours after the shift. Although it reached 180 units/$10^5$ cells/day and then decreased slightly after that, it continued to remain at a high level (125 units/$10^5$ cells/day).

These findings indicated that shifting to a lower temperature is effective in AE production by batch culture.

Example 3

Application of Low Temperature Culture to Continuous Culture

The efficacy of low temperature culture in batch culture was confirmed by Example 2. Next, this experiment was conducted to examine the application of low temperature culture to continuous culture.

Figure 13:
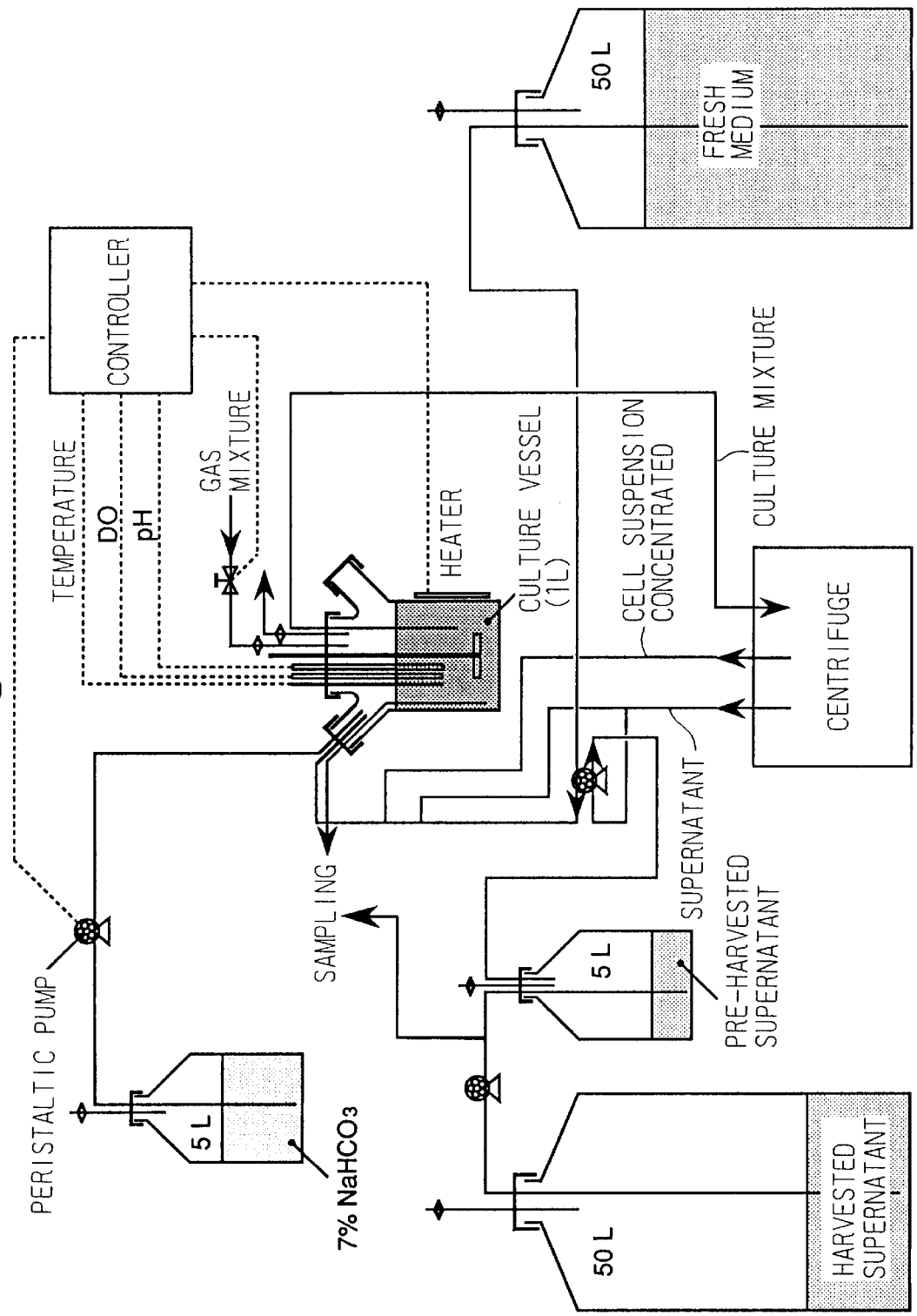
FIG. 13 is a flow chart of the culture system used in the continuous culture described in Example 3.

The culture system shown in FIG. 13 was constructed in order to perform continuous culture. A continuous centrifugal separator was used to prepare a cell concentrate (suspension) used to perform perfusion and to separate the culture supernatant.

3μ-1S cells, subcultured in 300 mL Erlenmeyer flasks, were inoculated into a 1 liter spinner flask within the above-mentioned culture system to make a cell density of $2\times10^5$ cells/mL and culture volume of 800 mL, followed by the start of preculturing. Perfusion was started when the cell density reached $1\times10^6$ cells/mL. Perfusion rate was then increased corresponding to cell growth, and preculture was performed until cell density reached $6\times10^6$ cells/mL. Furthermore, culture temperature was controlled to 37° C., DO at 60% air saturation, and pH at 7.2. In addition, the stirring rate of the spinner flask was adjusted to 100 rpm. Next, the culture was divided into two portions to examine the effects of low temperature culture (inoculated cell density: $3\times10^6$ cells/mL). Using two sets of the above-mentioned culture system, culture was started under the same conditions as preculture. Using a perfusion rate of 4.5 culture volume/day, the culture temperature of one of the culture vessels was shifted from 37° C. to 34° C. when cell density again reached 6×106 cells/mL to investigate the effect of low temperature culture. Furthermore, with the exception of culture temperature, the same culture conditions were used for both incubation temperatures. Those results are shown in FIG. 14.

Figure 14A:
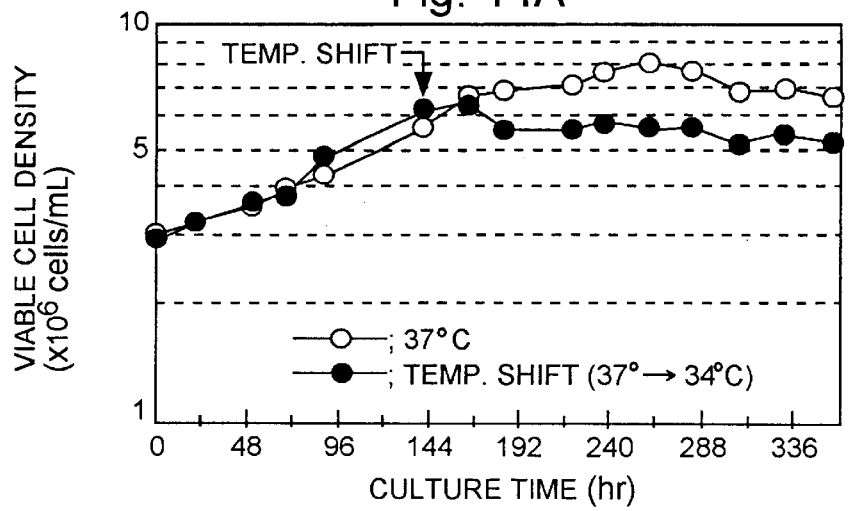
FIG. 14 shows the effects of a temperature shift from 37° C. to 34° C. during continuous culture of 3μ-1S cells. (A) shows the changes with time elapsing in cell density, (B) shows the changes with time elapsing in AE production per culture vessel per day, and (C) shows the changes with time elapsing in cellular productivity of AE.

FIG. 14(A) shows the changes in cell density. Equal cell growth was exhibited by both culture vessels until cell density reached $6\times10^6$ cells/mL. After the temperature was shifted from 37° C. to 34° C., cell density became steady at 6 to $8\times10^6$ cells/mL under the conditions of this experiment. Furthermore, cell viability was maintained at 90% and above in both cultures. In addition, glucose consumption during culture at 34° C. decreased in comparison with that at 37° C.

Figure 14B:
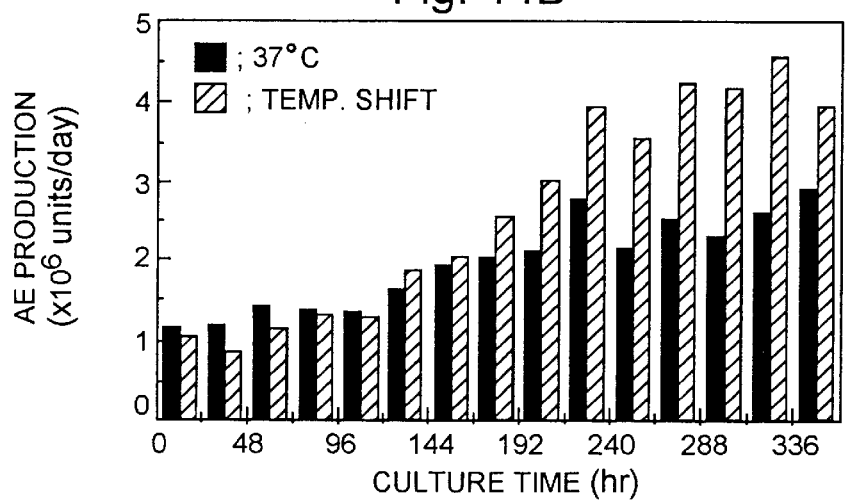
Figure 14C:
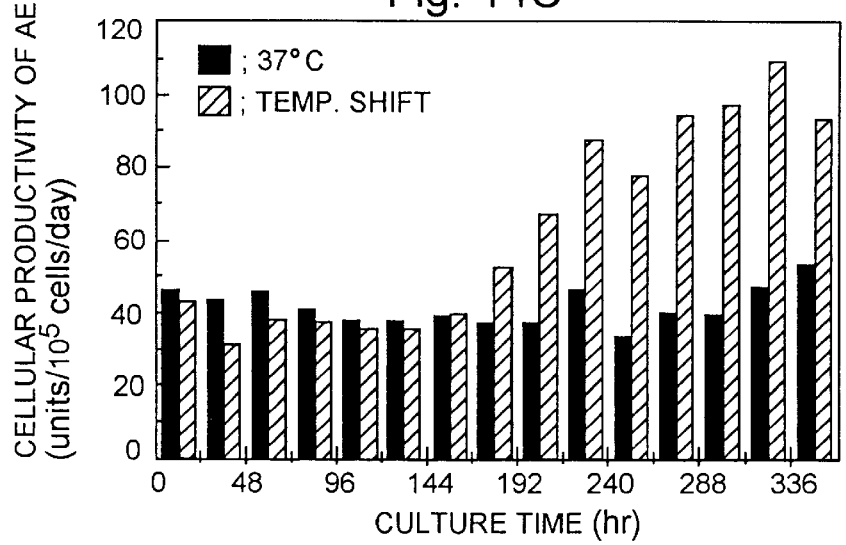

As shown in FIGS. 14(B) and (C), application of low temperature culture to high-density culture was effective, resulting in increases in both AE production per vessel and cellular productivity of AE. In comparison with culture at 37° C., AE production per vessel increased roughly 1.6 times, reaching $4\times10^6$ units/day (FIG. 14(B), equivalent to 27 times the amount in the case of batch culture at 37° C. using the same culture volume), while cellular productivity of AE increased roughly 2.5 times, reaching 100 units/$10^5$ cells/day (FIG. 14(C)). In addition, since there was no decrease in cellular productivity of AE observed accompanying increasing cell density (see Embodiment 1), it is expected that AE production can be further increased as cell density increases.

On the basis of the above results, it was shown that culture at lower temperatures is also effective in continuous culture as well.

The present invention makes it extremely easy to increase the overall efficiency (reduced costs) of animal cell culture. Namely, lowering the culture temperature not only effectively enhances substance productivity, but also reduces medium consumption, and decreases impurities such as proteins derived from metabolic by-products and cell contents, and so forth. Thus, together with being able to realize a significant reduction in culture costs, it also enables costs to be reduced in the purification process as well. Additionally, performing culture at low temperatures is also advantageous in terms of energy conservation. Thus, the present invention is able to greatly contribute to substance production by culture of animal cells at all scales of production.

We claim:

1. A method for culturing recombinant animal cells, transformed or transfected with a vector prepared by in vitro gene recombination, wherein said recombinant animal cells are not temperature sensitive mutants, to increase production of a desired product, comprising the steps of:
   (1) culturing the recombinant animal cells at a temperature at which the animal cells can grow; and then (2) culturing the recombinant animal cells at a lower temperature.

2. A method according to claim 1 wherein said recombinant animal cells are recombinant cells that exhibit greater productivity of said desired product at the lower culturing temperature than at the temperature at which the animal cells can grow.

3. A method according to claim 2 wherein said recombinant animal cells are recombinant cells derived from homeothermic animals.

4. A method according to claim 3 wherein said recombinant animal cells are recombinant cells derived from mammals.

5. A method according to claim 4 wherein said recombinant animal cells are recombinant cells derived from rodents.

6. A method according to claim 5 wherein said recombinant animal cells are recombinant cells derived from CHO (Chinese hamster ovary) cell line.

7. A method according to claim 6 wherein said animal cells are recombinant cells established by the DHFR (dihydrofolate reductase) gene amplification system.

8. A method according to claim 7 wherein said animals cells are recombinant CHO cells that produce amidating enzymes.

9. A method according to claim 1, wherein said lowered culturing temperature is less than about 37° C.

10. A method according to claim 1, wherein said temperature at which the animal cells can grow is between about 36 and 38° C.

11. A method according to claim 10 wherein said lowered culturing temperature is 30 to 35° C.

* * * * *